US011052132B2

(12) United States Patent
Arnold et al.

(10) Patent No.: US 11,052,132 B2
(45) Date of Patent: Jul. 6, 2021

(54) METHODS AND COMPOSITIONS FOR TREATING CYSTIC FIBROSIS

(71) Applicant: PHASEBIO PHARMACEUTICALS, INC., Malvern, PA (US)

(72) Inventors: Susan Arnold, Malvern, PA (US); David James Ballance, Malvern, PA (US)

(73) Assignee: PHASEBIO PHARMACEUTICALS, INC., Malvern, PA (US)

( * ) Notice: Subject to any disclaimer, the term of this patent is extended or adjusted under 35 U.S.C. 154(b) by 0 days.

(21) Appl. No.: 15/308,626

(22) PCT Filed: May 8, 2015

(86) PCT No.: PCT/US2015/029926
§ 371 (c)(1),
(2) Date: Nov. 3, 2016

(87) PCT Pub. No.: WO2015/172046
PCT Pub. Date: Nov. 12, 2015

(65) Prior Publication Data

US 2017/0182130 A1 Jun. 29, 2017

Related U.S. Application Data

(60) Provisional application No. 61/990,425, filed on May 8, 2014.

(51) Int. Cl.

| | |
|---|---|
| ***A61K 38/22*** | (2006.01) |
| ***A61K 31/404*** | (2006.01) |
| ***A61K 31/443*** | (2006.01) |
| ***A61K 31/47*** | (2006.01) |
| ***A61K 38/39*** | (2006.01) |
| ***A61K 45/06*** | (2006.01) |

(52) U.S. Cl.
CPC ........ *A61K 38/2278* (2013.01); *A61K 31/404* (2013.01); *A61K 31/443* (2013.01); *A61K 31/47* (2013.01); *A61K 38/39* (2013.01); *A61K 45/06* (2013.01)

(58) Field of Classification Search
CPC .................................................. A61K 38/2278
See application file for complete search history.

(56) References Cited

U.S. PATENT DOCUMENTS

| | | | |
|---|---|---|---|
| 4,132,746 | A | 1/1979 | Urry et al. |
| 4,187,852 | A | 2/1980 | Urry et al. |
| 4,474,851 | A | 10/1984 | Urry |
| 4,500,700 | A | 2/1985 | Urry |
| 4,589,882 | A | 5/1986 | Urry |
| 4,605,641 | A | 8/1986 | Bolin et al. |
| 4,749,647 | A | 6/1988 | Thomas et al. |
| 4,752,638 | A | 6/1988 | Nowinski et al. |
| 4,783,523 | A | 11/1988 | Urry et al. |
| 4,870,055 | A | 9/1989 | Urry et al. |
| 4,898,926 | A | 2/1990 | Urry |
| 5,147,855 | A | 9/1992 | Gozes et al. |
| 5,234,907 | A | 8/1993 | Bolin |
| 5,235,041 | A | 8/1993 | Cappello et al. |
| 5,236,904 | A | 8/1993 | Gerstenberg et al. |
| 5,243,038 | A | 9/1993 | Ferrari et al. |
| 5,288,514 | A | 2/1994 | Ellman |
| 5,376,637 | A | 12/1994 | Sawai et al. |
| 5,428,015 | A | 6/1995 | Kurono et al. |
| 5,445,934 | A | 8/1995 | Fodor et al. |
| 5,447,912 | A | 9/1995 | Gerstenberg et al. |
| 5,496,712 | A | 3/1996 | Cappello et al. |
| 5,506,120 | A | 4/1996 | Yamamoto et al. |
| 5,514,581 | A | 5/1996 | Ferrari et al. |
| 5,519,004 | A | 5/1996 | Urry |
| 5,520,672 | A | 5/1996 | Urry |
| 5,527,610 | A | 6/1996 | Urry |
| 5,545,617 | A | 8/1996 | Dartt et al. |
| 5,624,711 | A | 4/1997 | Sundberg et al. |
| 5,641,648 | A | 6/1997 | Ferrari et al. |
| 5,681,816 | A | 10/1997 | Korman |
| 5,702,717 | A | 12/1997 | Cha et al. |
| 5,747,646 | A | 5/1998 | Hakimi et al. |
| 5,770,570 | A | 6/1998 | Paul et al. |
| 5,770,697 | A | 6/1998 | Ferrari et al. |
| 5,773,249 | A | 6/1998 | Cappello et al. |
| 5,816,259 | A | 10/1998 | Rose |
| 5,830,713 | A | 11/1998 | Ferrari et al. |

(Continued)

FOREIGN PATENT DOCUMENTS

| | | | |
|---|---|---|---|
| JP | 2009-525946 | A | 7/2009 |
| WO | WO 1996/032406 | A1 | 10/1996 |

(Continued)

OTHER PUBLICATIONS

Alcolado et al., 2011, VIP-dependent increase in F508del-CFTR membrane localization is mediated by PKCe, Am J Physiol Cell Physiol, 301: C53-C65.*
Mathioudakis et al., 2013, Vasoactive Intestinal Peptide Inhaled Agonists: Potentail Role in Respiratory Therapeutics, Hippokratia, 17(1): 12-16.*
Chappe et al., 2008, Vasoactive Intestinal Peptide Increases Cystic Fibrosis Transmembrane Conductance Regulator Levels in the Apical Membrane of Calu-3 Cells through a Protein Kinase C-Dependent Mechanism, The Journal of Pharmacology and Experimental Therapeutics, 327(1): 226-238.*
Choi et al., 2007, Synergistic airway gland mucus secretion in response to vasoactive intestinal peptide and carbachol is lost in cystic fibrosis, The Journal of Clinical Investigation, 117(10): 3118-3127.*

(Continued)

*Primary Examiner* — Amber D Steele
(74) *Attorney, Agent, or Firm* — Cooley LLP

(57) ABSTRACT

The present disclosure provides a method of treating diseases or disorders associated with CFTR protein dysfunction, including Cystic Fibrosis, by administering stable, long-lasting vasoactive intestinal peptide therapeutic agents. These agents include one or more elastin-like peptides and can be administered at a low-dose.

16 Claims, 10 Drawing Sheets

Specification includes a Sequence Listing.

(56) References Cited

U.S. PATENT DOCUMENTS 5,854,387 A 12/1998 Urry et al.
5,900,405 A 5/1999 Urry
5,958,881 A 9/1999 Korman
5,972,406 A 10/1999 Urry et al.
5,972,883 A 10/1999 Gozes et al.
5,998,588 A 12/1999 Hoffman et al.
6,004,782 A 12/1999 Daniell et al.
6,018,030 A 1/2000 Ferrari et al.
6,037,321 A 3/2000 Cox et al.
6,063,061 A 5/2000 Wallace et al.
6,140,072 A 10/2000 Ferrari et al.
6,153,655 A 11/2000 Martinez et al.
6,184,348 B1 2/2001 Ferrari et al.
6,200,598 B1 3/2001 Needham
6,258,562 B1 7/2001 Salfield et al.
6,328,996 B1 12/2001 Urry
6,329,209 B1 12/2001 Wagner et al.
6,355,776 B1 3/2002 Ferrari et al.
6,380,154 B1 4/2002 Cappello et al.
6,429,188 B1 8/2002 Perez et al.
6,503,534 B1 1/2003 Pellet et al.
6,537,521 B2 3/2003 Uzgiris
6,541,033 B1 4/2003 Shah
6,582,926 B1 6/2003 Chilkoti
6,593,394 B1 7/2003 Li et al.
6,699,294 B2 3/2004 Urry
6,852,834 B2 2/2005 Chilkoti
6,998,387 B1 2/2006 Goke et al.
7,084,243 B2 8/2006 Glaesner et al.
7,094,755 B2 8/2006 Burman et al.
7,101,843 B2 9/2006 Glaesner et al.
7,138,486 B2 11/2006 Habener et al.
7,141,547 B2 11/2006 Rosen et al.
7,144,863 B2 12/2006 DeFelippis et al.
7,176,278 B2 2/2007 Prior
7,226,910 B2 6/2007 Wilson et al.
7,232,879 B2 6/2007 Galloway et al.
7,259,233 B2 8/2007 Dodd et al.
7,271,149 B2 9/2007 Glaesner et al.
7,332,473 B2 2/2008 Onoue et al.
7,364,859 B2 4/2008 Chilkoti
7,429,458 B2 9/2008 Chilkoti
7,442,680 B2 10/2008 Yong et al.
7,459,441 B2 12/2008 Minagawa et al.
7,468,353 B2 12/2008 Bevec
7,566,691 B2 7/2009 Nestor
7,582,608 B2 9/2009 Bokvist et al.
7,709,227 B2 5/2010 Dagher
7,723,472 B2 5/2010 Szoka
7,776,815 B2 8/2010 Vanderby et al.
8,178,495 B2 5/2012 Chilkoti
8,334,257 B2 12/2012 Chilkoti
8,367,626 B2 * 2/2013 Furgeson ........... A61K 47/6435
514/44 R
8,729,018 B2 5/2014 Chilkoti
9,029,505 B2 * 5/2015 Sadeghi ............. A61K 38/2278
530/350
9,458,218 B2 10/2016 Chilkoti
9,561,262 B2 2/2017 Georgopoulos et al.
9,700,598 B2 * 7/2017 Sadeghi ................. A61K 38/39
2001/0034050 A1 10/2001 Chilkoti
2002/0045567 A1 4/2002 Cappello et al.
2002/0099003 A1 7/2002 Wilson et al.
2002/0151458 A1 10/2002 Gomariz et al.
2003/0059840 A1 3/2003 Chilkoti
2003/0059841 A1 3/2003 Chilkoti
2003/0158092 A1 * 8/2003 Kai ........................ C07K 14/47
536/23.1
2004/0063631 A1 4/2004 Block
2004/0110296 A1 6/2004 Vargeese et al.
2004/0234609 A1 11/2004 Collier et al.
2005/0118109 A1 6/2005 Block et al.
2005/0203009 A1 9/2005 Pan et al.
2005/0255554 A1 11/2005 Chilkoti
2006/0165679 A1 * 7/2006 Golz ...................... G01N 33/74
424/133.1
2006/0247156 A1 11/2006 Vanderby et al.
2007/0009602 A1 1/2007 Setton et al.
2007/0265197 A1 11/2007 Furgeson et al.
2007/0293429 A1 * 12/2007 Nestor .................... A61P 39/00
514/1.7
2008/0085860 A1 4/2008 Bokvist et al.
2008/0096807 A1 * 4/2008 Bolin ...................... A61P 11/06
514/13.1
2008/0096811 A1 * 4/2008 Bokvist ............ C07K 14/57563
514/7.3
2008/0108573 A1 5/2008 Duggan
2008/0207492 A1 8/2008 Polt et al.
2008/0214440 A1 * 9/2008 Nestor ...................... A61P 3/04
514/1.1
2008/0221041 A1 9/2008 Block et al.
2008/0261863 A1 10/2008 Whelan et al.
2008/0274961 A1 11/2008 Bevec
2008/0312156 A1 12/2008 Setton et al.
2008/0318845 A1 12/2008 Bokvist et al.
2008/0318865 A1 12/2008 Juul-Mortensen
2009/0004104 A1 1/2009 Chilkoti
2009/0005315 A1 1/2009 Duggan
2009/0092582 A1 4/2009 Bogin et al.
2009/0170775 A1 * 7/2009 Nestor, Jr. ........ C07K 14/57563
514/1.1
2009/0175821 A1 7/2009 Bridon et al.
2009/0220455 A1 9/2009 Chilkoti
2009/0270317 A1 10/2009 Chilkoti
2010/0016212 A1 1/2010 Rubin et al.
2010/0022455 A1 1/2010 Chilkoti
2010/0184651 A1 7/2010 Maithal et al.
2010/0256044 A1 * 10/2010 Roth-Chiarello ............................
C07K 14/57563
514/1.8
2011/0039776 A1 2/2011 Chilkoti
2011/0053854 A1 3/2011 Fallon et al.
2011/0110916 A1 5/2011 Worman et al.
2011/0123487 A1 5/2011 Chilkoti
2011/0178017 A1 * 7/2011 Sadeghi .................... A61P 9/00
514/13.1
2011/0219462 A1 9/2011 Delbeck et al.
2011/0236384 A1 9/2011 Setton et al.
2013/0065816 A1 * 3/2013 Coy ....................... A61K 33/24
514/1.4
2013/0079277 A1 3/2013 Chilkoti
2013/0085099 A1 4/2013 Chilkoti
2013/0116184 A1 5/2013 Nichols et al.
2013/0143802 A1 6/2013 Chilkoti
2013/0150291 A1 6/2013 Jowett et al.
2013/0172274 A1 7/2013 Chilkoti
2013/0230581 A1 9/2013 Feng et al.
2013/0310329 A1 * 11/2013 Maiuri ................. A61K 31/047
514/25
2013/0310538 A1 11/2013 Chilkoti
2013/0315878 A1 11/2013 Feng et al.
2014/0024600 A1 1/2014 Chilkoti et al.
2014/0039053 A1 2/2014 Ohnishi
2014/0073667 A1 3/2014 Morgan
2014/0088141 A1 3/2014 Binch et al.
2014/0100155 A1 * 4/2014 Madden ................... C07K 7/06
514/1.8
2014/0171370 A1 6/2014 Arnold et al.
2014/0213516 A1 7/2014 Chilkoti
2014/0364371 A1 12/2014 Setton et al.
2015/0111829 A1 4/2015 Georgopoulos et al.
2016/0220642 A1 8/2016 Sadeghi et al.
2017/0072021 A1 3/2017 Georgopoulos et al.
2018/0008677 A1 1/2018 Sadeghi et al.
2018/0333467 A1 11/2018 Georgopoulos et al.

FOREIGN PATENT DOCUMENTS

WO WO 2007/057922 A1 5/2007
WO WO 2007/065226 A1 6/2007
WO WO 2007/073486 A2 6/2007
WO WO 2008/030968 A2 3/2008

(56) References Cited

FOREIGN PATENT DOCUMENTS

| | | |
|---|---|---|
| WO | WO 2010/080578 A1 | 7/2010 |
| WO | WO 2011/020091 A1 | 2/2011 |
| WO | WO 2012/170524 A1 | 12/2012 |
| WO | WO 2013/177428 A1 | 11/2013 |
| WO | WO 2014/081849 A1 | 5/2014 |
| WO | WO 2014/113434 A1 | 7/2014 |
| WO | WO 2015/172046 A1 | 11/2015 |
| WO | WO 2016/081884 A2 | 5/2016 |
| WO | WO 2016/130518 A2 | 8/2016 |

OTHER PUBLICATIONS

Savage et al., 1990, Cystic fibrosis, vasoactive intestinal polypeptide, and active cutaneous vasodilation, J Appl Physiol, 69(6): 2149-2154.*

Chastre et al., 1989, Vasoactive intestinal peptide and its receptors in fetuses with cystic fibrosis, Am J Physiol, 257(4pt1): G561-G569.*

Qu et al., 2011, Activation of CFTR Trafficking and Gating by Vasoactive Intestinal Peptide in Human Bronchial Epithelial Cells, Journal of Cellular Biochemistry, 112: 902-908.*

Amruthwar et al., 2012, Preparation and characterization of elastin-like polypeptide scaffolds for local delivery of antibiotics and proteins, J Mater Sci: Mater Med, 23: 2903-2912.*

Christensen et al., 2013, Predicting Transition Temperatures of Elastin-Like Polypeptide Fusion Proteins, Biomacromolecules, 14(5) : 1514-1519.*

Langer et al., 2004, Hexanoylation of a VPAC2 receptor-preferring ligand markedly increased its selectivity and potency, Peptides, 25: 275-278.*

Burian et al., 2010, Vasoactive intestinal peptide (VIP) receptor expression in monocyte-derived macrophages from COPD patients, Peptides, 31:603-608.*

Onoue et al., 2004, Long-acting analogue of vasoactive intestinal peptide, [R15,20,21,L17]-VIP-GRR (IK312532), protects rat alveolar L2 cells from the cytotoxicity of cigarette smoke, Regulatory Peptides, 123: 193-199.*

Groneberg et al., 2006, Novel concepts of neuropeptide-based drug therapy: Vasoactive intestinal polypeptide and its receptors, European Journal of Pharmacology, 533: 182-194.*

Laburthe et al., 2002, VPAC Receptors for VIP and PACAP, Receptors and Channels, 8: 137-153.*

Moreno et al., 2000, Development of selective agonists and antagonists for the human vasoactive intestinal polypeptide VPAC2 receptor, Peptides, 21: 1543-1549.*

Igarashi et al., 2005, Development of Simplified Vasoactive Intestinal Peptide Analogs with Receptor Selectivity and Stability for Human Vasoactive Intestinal Peptide/Pituitary Adenylate Cyclase-Activating Polypeptide Receptors, The Journal of Pharmacology and Experimental Therapeutics, 315(1): 370-381.*

Summers et al., 2003, A Lymphocyte-Generated Fragment of Vasoactive Intestinal Peptide with VPAC1 Agonist Activity and VPAC2 Antagonist Effects, The Journal of Pharmacology and Experimental Therapeutics, 306(2): 638-645.*

Juarranz et al., 1999, Vasoactive intestinal polypeptide VPAC1 and VPAC2 receptor chimeras identify domains responsible for the specificity of ligand binding and activation, Eur J Biochem, 265: 449-456.*

Burian et al., 2012, Clinical Potential of VIP by Modified Pharmacokinetics and Delivery Mechanisms, Endocrine, Metabolic & Immune Disorders—Drug Targets, 12: 344-350.*

Mathioudakis et al., 2013, Vasoactive Intestinal Peptide Inhaled Agonists: Potential Role in Respiratory Therapeutics, Hippokratia, 17(1): 12-16.*

Miotto et al., 2004, Vasoactive intestinal peptide receptors in the airways of smokers with chronic bronchitis, Eur Respir J, 24: 958-963.*

Nicole et al., 2000, Identification of Key Residues for Interaction of Vasoactive Intestinal peptide with Human VPAC1 and VPAC2 Receptors and Development of a Highly Selective VPAC1 Receptor Agonist, The Journal of Biological Chemistry, 275(31): 24003-24012.*

Sharma et al., 1995, The Distribution and Density of Airway Vasoactive Intestinal Polypeptide (VIP) Binding Sites in Cystic Fibrosis and Asthma, Pulmonary Pharmacology, 8: 91-96.*

Ameen and Robson, "Experimental Models of Duchenne Muscular Dystrophy: Relationship with Cardiovascular Disease." Open Cardiovasc Med J. (2010); 4: 265-277.

EP Application No. EP 15789718.2, Extended European Search Report dated Oct. 27, 2017, 8 pages.

Hinkle, et al., "Activation of the vasoactive intestinal peptide 2 receptor modulates normal and atrophying skeletal muscle mass and force." Journal of Applied Physiology (2005); 98(2): 655-662.

Kowalczyk, T., et al., "Elastin-like polypeptides as a promising family of genetically-engineered protein based polymers." World Journal of Microbiology and Biotechnology (2014); 30(8): 2141-2152.

Massodi, et al., "Application of Thermally Responsive Elastin-like Polypeptide Fused to a Lactoferrin-derived Peptide for Treatment of Pancreatic Cancer." Molecules (2009); 14(6): 1999-2015.

PCT/US2016/017102, International Preliminary Report on Patentability, dated Aug. 15, 2017, 14 pages.

PCT/US2016/017102, International Search Report and Written Opinion, dated Aug. 11, 2016, 19 pages.

Rafferty, et al., "Rescue of Functional F508del Cystic Fibrosis Transmembrane Conductance Regulator by Vasoactive Intestinal Peptide in the Human Nasal Epithelial Cell Line JME/CF15." Journal of Pharmacology and Experimental Therapeutics (2009); 331(1): 2-13.

Tan, et al., "Recent developments in liposomes, microparticles and nanoparticles for protein and peptide drug delivery." Peptides (2010); 31(1): 184-193.

Delgado et al., "The significance of vasoactive intestinal peptide in immunomodulation", Pharmacological Reviews, 56(2): 249-290 (2004).

Domschke et al., "Vasoactive Intestinal Peptide in Man: Pharmacokinetics, Metabolic and Circulatory Effects," Gut, 19: 1049-1053 (1978).

Duggan, K.D. et al., "Effects of enalapril on vasoactive intestinal peptide metabolism and tissue levels", European Journal of Pharmacology, 358(1): 25-30 (1998).

Dvoráková, Magdalena Chottová. "Cardioprotective role of the VIP signaling system." Drug News Perspect (2005); 18(6): 387-391.

EP Application No. EP 10808864.1, Extended European Search Report dated Feb. 21, 2013, 6 pages.

EP Application No. EP 12796397.3, Extended European Search Report, dated Dec. 11, 2014, 9 pages.

Free et al. "A Phase 1, Multi-center, Randomized, Double-blind, Placebo Controlled Study to Evaluate the Safety/Tolerability, Pharmacokinetic and Hemodynamic Response Following Single Ascending Subcutaneous Doses of PB 1046 (Vasomera™) in Subjects with Essential Hypertension (Trial Registry No. NCT01523067)," PhaseBio Pharmaceuticals, p. 1, Nov. 2014. Retrieved from the Internet:<http://phasebio.com/wp-content/uploads/2014/12/AHAPresentation-FINAL-V1-12NOV2014.pdf> on Aug. 7, 2015 (Aug. 7, 2015). entire document, 1 page.

Gourlet et al., "Vasoactive Intestinal Peptide (VIP) and Pituitary Adenylate Cyclase-Activating Peptide (PACAP-27, but not PACAP-38) Degradation by the Neutral Endopeptidase EC 3.4.24.11," Biochemical Pharmacology, 54: 509-515 (1997).

Izumi et al., "Effect of Amino Terminal Methionine Residue on the Physicochemical Properties and Biological Activity of Recombinant Methionyl Human Interleukin-2 (S-6820)", Basic and Clinical Researches, vol. 24, No. 2, pp. 151-175 (and English Summary) (1990).

Kalfin et al., "Protective role of intracoronary vasoactive intestinal peptide in ischemic and reperfused myocardium." J Pharmacol Exp Ther. (1994); 268(2): 952-958.

Kobayashi et al., "Degradation of Vasoactive Intestinal Polypeptide by Rabbit Gastric Smooth Muscle Membranes," Peptides, 15(2): 323-332 (1994).

(56) References Cited

OTHER PUBLICATIONS

Meyer et al. "Purification of Recombinant Proteins by Fusion with Thermally-Responsive Polypeptides", Nature Biotechnology, 17: 1112-1115 (1999).
Meyer et al., "Drug targeting using thermally responsive polymers and local hyperthermia," Journal of Controlled Release, 74: 213-224 (2001).
Meyer et al., "Polypeptide Fusion Tag for Thermal Purification of Recombinant Proteins," Abstracts of Papers, 217th ACS National Meeting, Anaheim, CA, US, Mar. 21-25, 1999, BIOT-078, see abstract.
Meyer et al., "Protein Purification by Fusion with an Environmentally Responsive Elastin-Like Polypeptide: Effect of Polypeptide Length on the Purification of Thioredoxin", Biotechnology Progress, 17: 720-728 (2001).
Meyer et al., "Targeting a Genetically Engineered Elastin-like Polypeptide to Solid Tumors by Local Hypothermia," Cancer Res. , 61(4): 1548-1554 (2001).
Mori et al., "Decreases in substance P and vasoactive intestinal peptide concentrations in plasma of stroke-prone spontaneously hypertensive rats." Japanese Heart Journal (1993); 34(6): 785-794.
Mow et al. "PhaseBio Pharmaceuticals Inc," pp. 1-28, Jun. 2013, entire document. Article Retrieved from the Internet:<http://phasebio.com/wp-content/uploads/2013/12/PhaseBio-Noncon-Jefferies-Presentation-2013.pdf> on Aug. 7, 2015 (Aug. 7, 2015). entire document, 28 pages.
Onoue et al., "Long-active analague of Vasoactive Intestinal Peptide, [R15, 20, 21, L17]-VIP-GRR (IK212532), Protects Rat Alveolar L2 Cells from the Cytotoxicity of Cigarette Smoke," Regulatory Peptides, 123: 193-199 (2004).
Onoue et al., "Physicochemical and pharmacological characterization of novel vasoactive intestinal peptide derivatives with improved stability." European Journal of Pharmaceutics and Biopharmaceutics (2009); 73(1): 95-101.
Onyüksel et al., "A Novel Formulation of VIP in Sterically Stabilized Micelles Amplifies Vasodilation in Vivo," Pharmaceutical Research, 16(1): 155-160 (1999).
Önyüksel et al., "Human VIP-α: A long-acting, biocompatible and biodegradable peptide nanomedicine for essential hypertension," Peptides, 27: 2271-2275 (2006).
PCT/US2010/045605, International Preliminary Report on Patentability dated Feb. 14, 2012, 7 pages.
PCT/US2010/045605, International Search Report dated Jan. 5, 2011, 7 pages.
PCT/US2010/045605, Written Opinion dated Jan. 5, 2011, 6 pages.
PCT/US2012/041092, International Preliminary Report on Patentability, dated Dec. 10, 2013, 5 pages.
PCT/US2012/041092, International Search Report and Written Opinion, dated Sep. 21, 2012, 7 pages.
PCT/US2015/029926, International Preliminary Report on Patentability, dated Nov. 8, 2016, 8 pages.
PCT/US2015/029926, International Search Report and Written Opinion, dated Aug. 25, 2015, 11 pages.
Petkov et al., "Vasoactive intestinal peptide as a new drug for treatment of primary pulmonary hypertension." The Journal of Clinical Investigation (2003); 111(9): 1339-1346.
Pozo et al., "Tuning Immune Tolerance With Vasoactive Intestinal Peptide: A New Therapeutic Approach for Immune Disorders", Peptides, 28(9): 1833-1846 (2007).
Rubinstein et al., "Intratracheal and subcutaneous liposomal VIP normalizes arterial pressure in spontaneously hypertensive hamsters," International Journal of Pharmaceutics, 316: 144-147 (2006).
Said et al., "Moderate pulmonary arterial hypertension in male mice lacking the vasoactive intestinal peptide gene." Circulation (2007); 115(10): 1260-1268.
Sejourne et al., "Development of a Novel Bioactive Formulation of Vasoactive Intestinal Peptide in Sterically Stabilized Liposomes," Pharmaceutical Research, 14(3): 362-365 (1997).
Suzuki et al., "Encapsulation of VIP into liposomes restores vasorelaxation in hypertension in situ," Am. J. Physiol., 271(40): H282-H287 (1996).
Unverferth et al., "Human and canine ventricular vasoactive intestinal polypeptide: decrease with heart failure." The Journal of Laboratory and Clinical Medicine (1986), 108(1): 11-16.
Uversky et al., "Structure and stability of recombinant protein depend on the extra N-terminal methionine residue: S6 permutein from direct and fusion expression systems", Biochimica et Biophysica Acta (BBA)—Protein Structure and Molecular Enzymology, 1432(2): 324-332 (1999).
Victor, Z. C., et al. "Vasopeptidase inhibition reverses myocardial vasoactive intestinal peptide depletion and decreases fibrosis in salt sensitive hypertension." European Journal of Pharmacology (2004); 485(1): 235-242.
Yang et al., "Enhanced Inhibition of Human Immunodeficiency Virus Type 1 by Met-Stromal-Derived Factor 1β Correlates with Down-Modulation of CXCR4", Journal of Virology, 73(6): 4582-4589 (1999).
Ye, V. Z. C., et al. "Myocardial vasoactive intestinal peptide and fibrosis induced by nitric oxide synthase inhibition in the rat." Acta Physiologica Scandinavica (2003); 179(4): 353-360.
EP Application No. 16749691.8, Extended European Search Report dated Jul. 20, 2018, 17 pages.
EP Application No. 17163446.2, Extended European Search Report dated Feb. 21, 2018, 7 pages.
Frottin et al. "The Proteomics of N-terminal Methionine Cleavage," Molecular & Cellular Proteomics 5.12 (2006) pp. 2336-2349.
"PhaseBio Announces Promising Pre-clinical Results for PB1046 in Models of Duchenne Muscular Dystrophy," Apr. 22, 2015, XP002781492, retrieved from https://phasebio.com/phasebio-announces-promising-pre-clinicalresults-for-pb1046-in-models-of-duchenne-muscular-dystrophy/ [retrieved on May 29, 2018].
Miyazaki et al., "Segmental Myocardial Strain of the Left Ventricle in Patients With Duchenne Muscular Dystrophy Using Two-Dimensional Speckle Tracking Echocardiography," J. Echocardiogr., (2008) vol. 6, No. 4, pp. 100-108.

* cited by examiner

METHODS AND COMPOSITIONS FOR TREATING CYSTIC FIBROSIS

CROSS REFERENCE TO RELATED APPLICATIONS

This application is a U.S. National Phase of International Application No.: PCT/US2015/029926, filed May 8, 2015, entitled "Methods and Compositions For Treating Cystic Fibrosis" and claims priority under 35 U.S.C. 119(c) to U.S. Provisional Application Ser. No. 61/990,425, filed May 8, 2014, entitled "Method For Treating Cystic Fibrosis" the contents of which are herein incorporated by reference in their entireties.

DESCRIPTION OF THE TEXT FILE SUBMITTED ELECTRONICALLY

The contents of the text file submitted electronically herewith are incorporated herein by reference in their entirety: a computer readable format copy of the sequence listing (filename: PHAS-030_01US_SeqList_ST25.txt, date recorded Nov. 3, 2016, file size 21 kilobytes)

BACKGROUND

Cystic Fibrosis is a chronic, progressive, and fatal genetic disorder afflicting approximately 1 in 2, 500 people worldwide. This disease is caused by loss of function mutations in the Cystic Fibrosis Transmembrane Conductance Regulator (CFTR) gene which codes for a cAMP-regulated anion channel expressed primarily at the apical plasma membrane of secretory epithelial cells in the airways, pancreas, intestine, and other tissues. Nearly 2000 mutations in the CFTR gene have been identified that produce the loss of function phenotype by impairing translation, cellular processing, and/or chloride channel gating, (Rowe and Verkman (2013)).

In addition to inherited mutations in the CFTR gene, environmental factors, such as cigarette smoke, can lead to acquired CFTR protein defects. The loss of function CFTR phenotype leads to impaired ion and water transport across the cell membrane. Consequently, the affected cells produce abnormally thick mucus which obstructs the airways and glands, leading to difficulty breathing, increased infection, infertility, tissue damage, and death.

Current therapies focus on alleviating the symptoms of CFTR protein dysfunction. However, therapies that correct the underlying CFTR protein defect are needed.

SUMMARY OF THE INVENTION

The present disclosure provides Vasoactive Intestinal Peptide (VIP) therapeutics to treat, delay, or ameliorate symptoms of CFTR protein dysfunction. The buildup of thick, sticky mucus in afflicted patients results in permanent tissue damage, including the formation of scar tissue (fibrosis). This tissue damage leads to severe patient impairment and death. Preventing, delaying, or ameliorating the formation of this thick, sticky mucus can treat CFTR protein dysfunction.

In some aspects, the present disclosure provides a method for treating cystic fibrosis comprising administering to a patient in need thereof a pharmaceutical composition comprising a Vasoactive Intestinal Peptide (VIP) and one or more elastin-like peptides (ELP).

In some aspects, the present disclosure provides a method for treating symptoms of CFTR protein dysfunction comprising administering to a patient in need thereof a pharmaceutical composition comprising a Vasoactive Intestinal Peptide (VIP) and one or more elastin-like peptides (ELP).

In some aspects, the present disclosure provides a method for increasing CFTR protein function in a patient in need thereof comprising administering a pharmaceutical composition comprising a Vasoactive Intestinal Peptide (VIP) and one or more elastin-like peptides (ELP).

In some aspects, the present disclosure provides a method for increasing CFTR function comprising administering to a patient with an acquired defect in CFTR function a pharmaceutical composition comprising a Vasoactive Intestinal Peptide (VIP) and one or more elastin-like peptides (ELP). In some aspects, the patient acquired a defect in CFTR function through smoking. In some aspects, the patient with an acquired defect in CFTR function has chronic obstructive pulmonary disease (COPD).

In some aspects, the present disclosure provides a method for increasing ion efflux rates in a the cells of a subject with CFTR protein dysfunction comprising administering to the patient a pharmaceutical composition comprising a Vasoactive Intestinal Peptide (VIP) and one or more elastin-like peptides (ELP).

In some aspects, the present disclosure provides a method for increasing respiratory rates in a subject with CFTR protein dysfunction comprising administering to the patient a pharmaceutical composition comprising a Vasoactive Intestinal Peptide VIP and one or more elastin-like peptides (ELP).

In some aspects, the present disclosure provides a method for decreasing sweat chloride concentration in a subject with CFTR protein dysfunction comprising administering to the patient a pharmaceutical composition comprising a Vasoactive Intestinal Peptide (VIP) and one or more elastin-like peptides (ELP).

DETAILED DESCRIPTION

Figure 1:
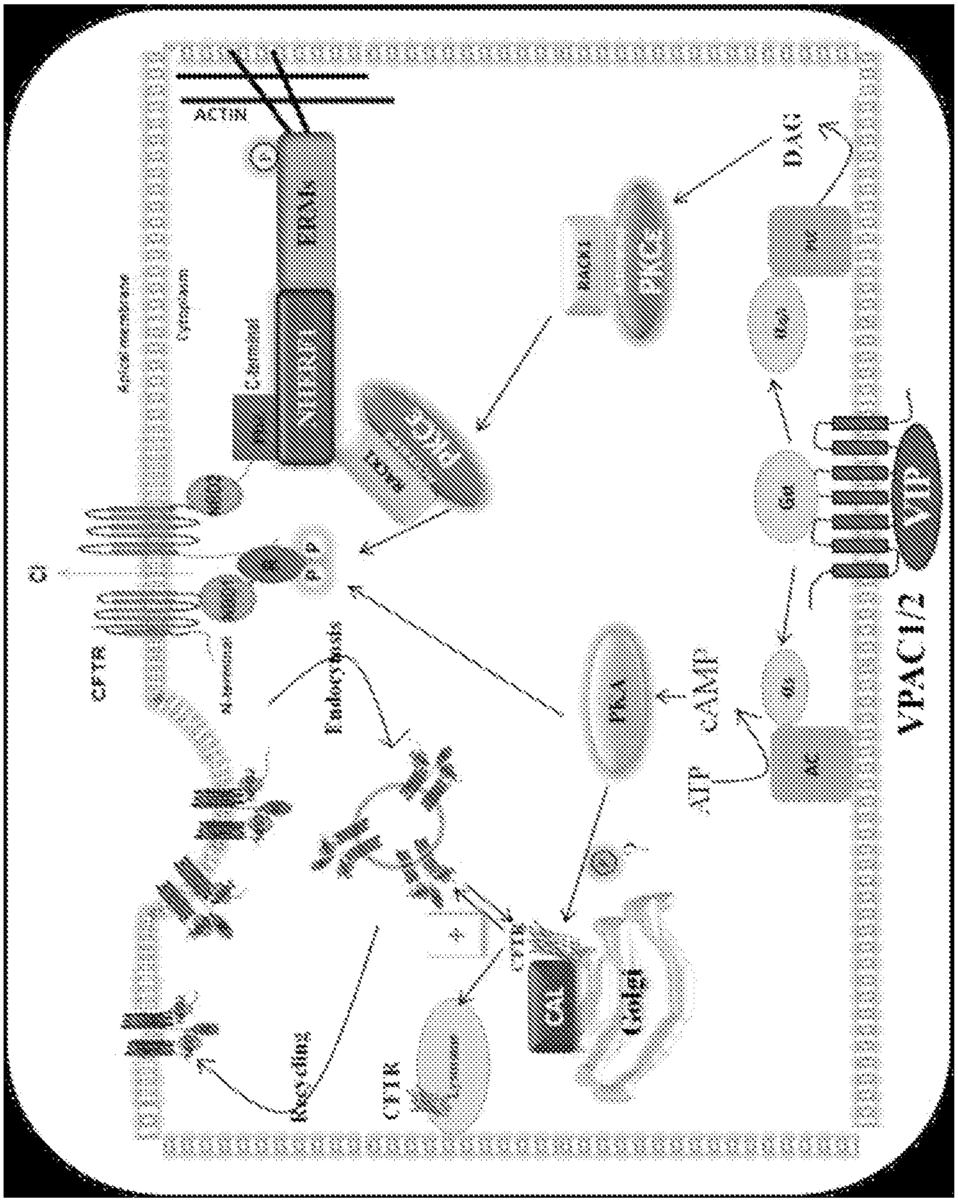
FIG. 1 is a schematic depicting the mechanism whereby VIP increases CFTR protein membrane density. (1) The dissociation of CFTR from CAL into the cytoplasm to promote CFTR membrane insertion; (2) Activation of the PKCε signaling cascade that potentiates NHERF1/PERMs complex interaction with membrane CFTR to mediate its surface stability (Alshafie (2014)).

Cystic Fibrosis (CF) is a recessive genetic disorder characterized by the buildup of thick, sticky mucus that leads to increased incidence of infections and tissue damage in afflicted patients. The disorder's most common symptoms include progressive damage to the respiratory system and chronic digestive problems. Cystic Fibrosis is caused by mutations in the Cystic Fibrosis Transmembrane Conductance Regulator (CFTR) gene that reduce or abolish the activity of the resulting protein. The CFTR protein is a transmembrane chloride channel primarily localized to the luminal, or apical membranes of epithelial cells in a variety of different tissues and organs including airway tissues, intestine, pancreas, kidney, vas deferens, and sweat duct.

Currently nearly 2,000 mutations in the CFTR gene have been identified that lead to a loss of function phenotype. For example, the F508del mutation, which is present in at least one allele in about 90% of Cystic Fibrosis patients, impairs CFTR folding, stability at the endoplasmic reticulum, and chloride channel gating (Rowe and Verkman (2013). Other identified mutations alter, for ample, channel gating (e.g. G551D), conductance (e.g. R117H), or translation (e.g. G542X).

Subjects can also acquire a defect in CFTR protein function (e.g. through smoking). For example, cigarette smoking inhibits chloride transport in cultured bronchial epithelial cells, and reduced. CFTR activity is observed in smokers without mutations in the CFTR gene (Sloane (2012). A number of extrapulmonary disorders associated with CFTR dysfunction are also found in smokers, including idiopathic pancreatitis, male infertility, cachexia, and diabetes mellitus (Raju (2013)).

The loss of function CFTR phenotype decreases the movement of chloride ions across the cell membrane, leading to aberrant ion and fluid homeostasis at epithelial surfaces, and damage to numerous organs and tissue systems. For example, in the lung, the defect in chloride transport is coupled with hyperabsorption of sodium, leading to the generation of thick and dehydrated mucus which allows chronic bacterial infections, and causes bronchiectasis and progressive airway destruction, eventually leading to the loss of pulmonary function. In the pancreas, the altered transport of electrolytes leads to decreased production of sodium bicarbonate and a buildup of mucus which blocks the pancreatic ducts. This blockage prevents digestive enzymes from exiting the pancreas causing digestive issues, and also tissue damage and fibrosis in the pancreas itself. In Cystic Fibrosis patients, pancreatic fibrosis can decrease the production of insulin, leading to Cystic Fibrosis-related diabetes mellitus. In the intestines, the altered ion and water transport leads to chronic digestive problems, diarrhea, and distal intestinal obstruction syndrome.

Vasoactive Intestinal Peptide (VIP) stimulates water and chloride transport across epithelial surfaces (Heinz-Erian (1985)) and was recently discovered to play a role in regulating CFTR protein stability (Chappe and Said (2012)). Prolonged VIP exposure can rescue F508delta-CFTR trafficking to the apical cell membrane and restore protein function (Chappe and Said (2012)). In the airway submucosal gland epithelial cell line Calu-3, VIP binding to one of its receptors, VPAC1, stimulates CFTR-dependent chloride secretion through activation of both PKA- and PKC-dependent signaling pathways (Chappe (2008); Derand (2004)). This signaling cascade results in CFTR protein being anchored to the actin cytoskeleton, thereby maintaining the protein at the membrane and reducing its endocytosis (Chappe and Said (2012)). As a protein that has effects on correcting CFTR function, VIP is an attractive therapeutic to treat diseases or disorders associated with CFTR protein dysfunction, however, VIP's poor stability after systemic administration (e.g. half-life of ≤1 minute in circulation) has limited its clinical application.

The present disclosure provides a method of preventing, delaying, or ameliorating the onset or progression of symptoms of CFTR protein dysfunction in subjects by administering Vasoactive Intestinal Peptide (VIP) therapeutics.

Vasoactive Intestinal Peptides

Vasoactive intestinal peptide (VIP) is a 28 amino acid neuropeptide which binds to two receptors, VPAC1 and VPAC2, found in a variety of tissues including the airway, small intestine, testes, and pancreas. VIP and its functionally and structurally related analogs are known to have many physiological functions, including, relaxing airway smooth muscle thereby acting as a bronchodilator, stimulating fluid secretion in airway submucosal glands, and regulating water and electrolyte secretion in the intestines and pancreas (Wine (2007); Wu (2011); Derand (2002)).

VIP-producing nerve fibers are co-localized with acetylcholine secreting neurons surrounding exocrine glands (Lundberg (1980); Heinz-Erian (1986)). In glands from subjects with functional CFTR protein, VIP induces fluid secretion, but this induction is impaired or absent in Cystic Fibrosis patients (Joo (2002); Joo (2012)). Further, in human and pig airway glands, administration of low concentrations of both VIP and acetylcholine stimulates the secretion mucus, but this synergism is lost in cystic fibrosis patients (Choi (2007)).

As shown in FIG. 1, VIP increases CFTR membrane insertion, stability, and function in human airway epithelial cells (Alshafie (2014)). In a murine VIP knockout model CFTR does not localize to the apical cell membrane, but instead remains mainly intracellular (Chappe and Said (2012)). The absence of CFTR from the apical membrane is associated with a lung pathology similar to that seen in Cystic Fibrosis patients, with inflammatory cell infiltration, thickening of the alveolar wall and the bronchiolar mucosa, and goblet cell hyperplasia. Administration of VIP intraperitoneally for three weeks restores CFTR apical membrane localization, and prolonged VIP stimulation increases the number of CFTR channels at the cell membrane (Chappe (2008)). This increase in apical CFTR density, which occurs via stabilization of CFTR at the membrane, is associated with an increase in CFTR-dependent function as measured by iodide efflux assays (Chappe (2008)).

In some aspects the disclosure provides therapeutic compositions that may include one or more various VIP peptides. For example, the VIP peptide may comprise or consist of a polypeptide having SEQ ID NO: 14, SEQ ID NO: 17, or SEQ ID NO: 19. In some embodiments, the present disclosure provides a VIP without the N-terminal Methionine (e.g. SEQ ID NO: 17). In some embodiments, the present disclosure provides a VIP with the N-terminal Methionine (e.g. SEQ ID NO: 14).

Mature human VIP has 28 amino acid residues with the following sequence: HSDAVFTDNYTRLRKQMAVKKYLNSILN (SEQ ID NO: 17). VIP results from processing of the 170-amino acid precursor molecule prepro-VIP. Structures of VIP and exemplary analogs have been described in U.S. Pat. Nos. 4,835,252, 4,939,224, 5,141,924, 4,734,400, 4,605,641, 6,080,837, 6,316,593, 5,677,419, 5,972,883, 6,489,297, 7,094,755, and 6,608,174.

A number of mutations to improve peptide stability against proteases etc. are detailed in the literature (see Onune et al *Physicochemical and pharmacological characterization of novel vasoactive intestinal peptide derivatives with improved stability, Eur. Pharm. Biopharm.* 2009). For example, modified VIP peptides include the sequences of SEQ ID NOs: 14-19. In some aspects, the present disclosure provides modified VIP peptides that include one or more of these modifications. In some embodiments, the present disclosure provides modified VIP peptides that include one or more of these modifications and further include additional VIP modifications described herein.

In various embodiments, the present disclosure provides a modified VIP (e.g., comprising SEQ ID NO: 14) or a functional analog as described herein. Generally, functional analogs of VIP, include functional fragments truncated at the N- or C-terminus by from 1 to 10 amino acids, including by 1, 2, 3, or up to about 5 amino acids (with respect to SEQ ID NO: 14). Such functional analogs may contain from 1 to 5 amino acid insertions, deletions, and/or substitutions (collectively) with respect to the native sequence (e.g., SEQ ID NO: 17), and in each case retain the activity of the native peptide (e.g., through VPAC2 and/or VPAC1 binding). Such activity may be confirmed or assayed using any available assay, including an assay described herein, and including any suitable assay to determine or quantify an activity described in Delgado et al., *The Significance of Vasoactive intestinal Peptide in Immunomodulation, Pharmacol. Reviews* 56(2):249-290 (2004). In these or other embodiments, the VIP component of the modified VIP has at least about 50%, 75%, 80%, 85%, 90%, 95%, or 97% identity with the native mature sequence (SEQ ID NO: 17). The determination of sequence identity between two sequences (e.g., between a native sequence and a functional analog) can be accomplished using any alignment tool, including for example, that disclosed in Tatusova et al., *Blast* 2 *sequences—a new tool for comparing protein and nucleotide sequences, FEMS Microbiol Lett.* 174:247-250 (1999).

In various aspects, the present disclosure provides a modified VIP molecule having receptor preference for VPAC2 or VPAC1, as compared to unmodified VIP (e.g., a peptide consisting of the amino acid sequence of SEQ ID NO: 14). For example, the modified VIP may have a relative binding preference for VPAC2 over VPAC1 of at least about 2:1, about 5:1, about 10:1, about 25:1, about 50:1 about 100:1, about 500:1 or more. In other embodiments, the modified VIP may have a relative binding preference for VPAC1 over VPAC2 of at least about 2:1, about 5:1, about 10:1, about 2.5:1, about 0.50:1, about 100:1, about 500:1, or more. For example, in certain embodiments, the modified VIP activates the VPAC2 receptor with an EC50 within a factor of about 2 of mature, unmodified, human VIP (SEQ ID NO: 17). However, this same modified VIP is 50- or 100-fold or more less potent than mature, unmodified, human VIP in activating the \TACT receptor. In some embodiments, the modified VIP may have relatively equipotent binding preferences for VPAC1 and VPAC2.

Such modified VIP molecules may contain modified N-terminal regions, such as an addition of from 1 to about 500 amino acids to the N-terminal histidine of VIP, which may include heterologous mammalian amino acid sequences. For example, the modified VIP may contain a single methionine at the N-terminal side of the natural N-terminal histidine of mature VIP. This can be prepared in *E. coli* or other bacterial expression system, since the methionine will not be removed by *E coli* When the adjacent amino acid is histidine. Alternatively, the N-terminal amino acid may be any of the naturally-occurring amino acids, namely alanine, arginine, asparagine, aspartic acid, cysteine, glutamic acid, glutamine, glycine, histidine, isoleucine, leucine, lysine, methionine, phenylalanine, serine, threonine, tryptophan, tyrosine, valine, and proline.

The additional sequence added to the N-terminus of VIP may be of any sequence, including biologically active and biologically inert sequences of from 1 to about 100, 1 to about 50, 1 to about 20, 1 to about 10, and 1 to about 5 amino acids.

The N-terminus of the modified VIP may have the structure M-N, where M is methionine, and N is the N-terminus of the VIP molecule (e.g., SEQ ID NO. 14). This methionine supports translation of the protein in a bacterial or eukatyatic host cell. Thus, the modified VIP can be made in a biological system, including bacterial and yeast expression systems (e.g., *E. coli*). While methionine can sometimes be removed by methionine aminopeptidase (MA) in bacterial expression systems, histidine (H) is one of the least favored residues at position 2 for MA.

The half-life of protein therapeutics can be extended by a variety of means, including increasing the size and thus the hydrodynamic volume of the protein therapeutic, adding modified or unnatural amino acids, conjugation of moieties pegylation), the addition of synthetic sequences (e.g. XTEN® sequences, PASylation®), carboxy-terminal extension from hCG (CTP), addition of albumin-binding sequences (e.g. AlbudAb®), conjugation of albumin-binding fatty acids, and post-translational modifications such as N-glycosylation and fusion to other peptides. In still other embodiments, VIP is modified by fusion with a mammalian heterologous protein, such as a mammalian protein effective for extending half-life of therapeutic molecules. Such sequences may be mammalian sequences, such as albumin, transferrin, or antibody Fc sequences. Such sequences are described in See U.S. Pat. No. 7,238,667 (particularly with respect to albumin conjugates), U.S. Pat. No. 7,176,278 (particularly with respect to transferrin conjugates), and U.S. Pat. No. 5,766,883. In some embodiments, the VIP is modified at the N-terminus. In some embodiments, the VIP is modified at the C-terminus.

In other embodiments, VIP is activatable by a peptidase or protease, such as an endogenous peptidase or protease. Such activatable sequences are described in International Application No. PCT/US2009/068656. As used herein, the terms "peptidase" and "protease" are interchangeable. For example, the VIP may be designed to be activatable by a dipeptidyl peptidase. Exemplary dipeptidyl peptidases include dipeptidyl peptidase-1 (DPP-I), dipeptidyl peptidase-3 (DPP-III), dipeptidyl peptidase-4 (DPP-IV), dipeptidyl peptidase-6 (DPP-VI), dipeptidyl peptidase-7 dipeptidyl peptidase-8 (DPP-VIM dipeptidyl peptidase-9 (DPP-IX), dipeptidyl peptidase-10 (DPP-X). Substrate sequences for such dipeptidases are known.

In some embodiments, the N-terminus of an activatable VIP may have the structure Z-N, where Z is a substrate for a dipeptidase Z is removed by dipeptidase exposure), and N is the N-terminus of VIP. The activatable VIP may have an N-terminal sequence with the formula M-X-N where M is methionine, X is Pro, Ala, or Ser, and N is the N-terminal of VIP or VIP analog. In this manner, M and X will be sensitive to, and removed by a host cell (e.g., *E. coli.*), and/or a dipeptidase (e.g., DPP-IV), subsequently. Alternatively, the N-terminal sequence of the activatable VIP may be X1-X2-N, where X1 is Gly, Ala, Ser, Cys, Thr, Val, or Pro; X2 is Pro, Ala, or Ser; and N is the N-terminal of VIP. X1-X2 is a substrate for dipeptidase (e.g., DPP-IV), and dipeptidase digestion will expose N, the desired. N-terminus of the VIP or the VIP analog (e.g., SEQ ID NO. 16). In such embodiments, the protein may be produced by expression of a construct encoding M-X1-X2-N (where M is methionine) in a host cell (e.g., *E. coli.*), since Gly, Ala, Ser, Cys, Thr, Val, or Pro at the second position will signal the removal of the Met, thereby leaving X1-X2 on the N-terminus, which can be activated by a dipeptidase (e.g., DPP-IV) in vivo. In some embodiments, the peptidase may be present in the body and act on the activatable VIP after injection.

In other embodiments, the N-terminus of the modified activatable VIP has the structure M-Z-N, where M is methionine, Z is a substrate for a dipeptidase (e.g., Z is removed by dipeptidase exposure), and N is a non-His N-terminal of an active VIP (modified VIP). For example, the modified activatable VIP may have an N-terminal sequence with the formula M-X-N where M is methionine; X is Pro, Ala, or Ser; and N is a non-His N-terminal of the active VIP. In this manner, M and X will be sensitive to, and removed by a host cell (e.g., *E. coli.*), and/or a dipeptidase (e.g., DPP-IV), subsequently. Alternatively, the N-terminal sequence of the activatable VIP may be X1-X2-N, where X1 is Gly, Ala, Ser, Cys, Thr, Val, or Pro; X2 is Pro, Ala, or Ser; and N is a non-His N-terminal of the active VIP. X1-X2 is a substrate for dipeptidase (e.g., DPP-IV), and dipeptidase digestion will expose N, the desired non-His N-terminus of the VIP.

Still other embodiments, the N-terminus of a modified activatable VIP has the structure M-Z-S-N, where M is methionine; Z is a substrate for a dipeptidase Z is removed by dipeptidase exposure); N is the N-terminus of mature VIP (His); and S is one or more amino acids which will be exposed after dipeptidase digestion, and which provide a modified VIP as previously described. For example, the modified activatable VIP may have an N-terminal sequence with the formula M-X-S-N where M is methionine, X is Pro, Ala, or Ser; N is the N-terminal of mature VIP; and S is one or more amino acids which will be exposed after dipeptidase digestion, and will provide receptor preference. Alternatively, the N-terminal sequence of the activatable VIP may be X1-X2-S-N, where X1 is Gly, Ala, Ser, Cys, Thr, Val, or Pro; X2 is Pro, Ala, or Ser; N is a non-His N-terminal of VIP; and S is one or more amino acids which will be exposed after dipeptidase digestion. X1-X2 is a substrate for dipeptidase (e.g., DPP-IV), and dipeptidase digestion will expose S.

In some embodiments, N-terminal chemical modifications to the VIP N-terminus provides receptor preference. Chemical modification of proteins and methods thereof are well known in the art. Non-limiting exemplary chemical modifications are PEGylation, methylglyoxalation, reductive alkylation, performic acid oxidation, succinylation, aminoethylation, and lipidation (Clifton, New Protein Techniques, New Jersey: Humana Press, 1985. ISBX. 0-89603-126-8. Volume. 3 of. Methods in Molecular Biology). Chemical groups, such as PEGylation, may be attached by modifications of cysteine, methionine, histidine, arginine, tryptophan, tyrosine, carboxyl groups have been described previously (see Lundblad, Techniques in Protein Modification, CRC Press, 1995).

Elastin-Like Peptides

In some aspects the disclosure provides therapeutic compositions that include a Vasoactive Intestinal Peptide and one or more elastin-like peptides (ELP). In some embodiments, a VIP and one or more ELPs are fused together. In some embodiments, a VIP and one or more ELPs are produced as a recombinant fusion polypeptide. In some embodiments, the therapeutic composition includes a Vasoactive Intestinal Peptide and one or more ELPs as separate molecules. In yet other embodiments, the compositions include a VIP-ELP fusion protein and ELPs as separate molecules. In some embodiments, the compositions include SEQ ID NO: 15 (PB1046). In some embodiments, the compositions include SEQ ID NO: 20 (PB1120).

The ELP sequence includes structural peptide units or sequences that are related to, or mimics of, the elastin protein. The ELP sequence is constructed from structural units of from three to about twenty amino acids, or in some embodiments, from four to ten amino acids, such as four, five or six amino acids. The length of the individual structural units may vary or may be uniform. For example, structural units include units defined by SEQ ID NOS: 1-13, which may be employed as repeating structural units, including tandem-repeating units, or may be employed in some combination. Thus, the ELP includes essentially structural unit(s) selected from SEQ ID NOS: 1-13.

In some embodiments, the amino acid sequence of the ELP unit is from about 1 to about 500 structural units, or in certain embodiments about 9 to about 200 structural units, or in certain embodiments about 10 to 200 structural units, or in certain embodiments about 50 to about 200 structural units, or in certain embodiments from about 80 to about 200 structural units, or from about 80 to about 150 structural units, such as one or a combination of units defined by SEQ ID NOS: 1-13. Thus, the structural units collectively may have a length of from about 50 to about 2000 amino acid residues, or from about 100 to about 800 amino acid residues, or from about 200 to about 700 amino acid residues, or from about 400 to about 600 amino acid residues, or from about 500 to about 700 amino acid residues. In exemplary embodiments, the amino acid sequence of the ELP structural unit includes about 3 structural units, about 7 structural units, about 9 structural units, about 10 structural units, about 15 structural units, about 18 structural units, about 20 structural units, about 40 structural units, about 80 structural units, about 100 structural units, about 120 structural units, about 140 structural units, about 144 structural units, about 160 structural units, about 180 structural units, about 200 structural units, or about 500 structural units. In exemplary embodiments, the structural units collectively have a length of about 45 amino acid residues, of about 90 amino acid residues, of about 100 amino acid residues, of about 200 amino acid residues, of about 300 amino acid residues, of about 400 amino acid residues, of about 500 amino acid residues, of about 600 amino acid residues, of about 700 amino acid residues, of about 800 amino acid residues, or of about 1000 amino acid residues.

The ELP amino acid sequence may exhibit a visible and reversible inverse phase transition with the selected formulation. That is, the amino acid sequence may be structurally disordered and highly soluble in the formulation below a transition temperature (Tt), but exhibit a sharp (2-3° C. range) disorder-to-order phase transition when the temperature of the formulation is raised above the Tt. In addition to temperature, length of the amino acid polymer, amino acid composition, ionic strength, pH, pressure, temperature, selected solvents, presence of organic solutes, and protein concentration may also affect the transition properties, and these may be tailored in the formulation for the desired absorption profile. Absorption profile can be easily tested by determining plasma concentration or activity of the active agent over time.

In certain embodiments, the ELP component(s) may be formed of multipeptide structural units (e.g. tetrapeptides, pentapeptides, hexapeptides, octapeptides, or nonapeptides), including but not limited to:

(a) the tetrapeptide Val-Pro-Gly-Gly, or VPGG (SEQ ID NO: 1);
(b) the tetrapeptide Ile-Pro-Gly-Gly, or IPGG (SEQ ID NO: 2);
(c) the pentapeptide Val-Pro-Gly-X-Gly, or VPGXG (SEQ ID NO: 3) where X is any natural or non-natural amino acid residue, and where X optionally varies among polymeric or oligomeric repeats;
(d) the pentapeptide Ala-Val-Gly-Val-Pro, or AVGVP (SEQ ID NO: 4);
(e) the pentapeptide Ile-Pro-Gly-X-Gly, or IPGXG (SEQ ID NO: 5), where X is any natural or non-natural amino acid residue, and where X optionally varies among polymeric or oligomeric repeats; (e) the pentapeptide Ile-Pro-Gly-Val-Gly, or IPGVG (SEQ ID NO: 6);
(f) the pentapeptide Leu-Pro-Gly-X-Gly, or LPGXG (SEQ ID NO: 7), where X is any natural or non-natural amino acid residue, and where X optionally varies among polymeric or oligomeric repeats;
(g) the pentapeptide Leu-Pro-Gly-Val-Gly, or LPGVG (SEQ ID NO: 8);
(h) the hexapeptide Val-Ala-Pro-Gly-Val-Gly, or VAPGVG (SEQ ID NO: 9);
(i) the octapeptide Gly-Val-Gly-Val-Pro-Gly-Val-Gly, or GVGVPGVG (SEQ ID NO: 10);
(j) the nonapeptide Val-Pro-Gly-Phe-Gly-Val-Gly-Ala-Gly, or VPGFGVGAG (SEQ ID NO: 11);
(k) the nonapeptides Val-Pro-Gly-Val-Gly-Val-Pro-Gly-Gly, or VPGVGVPGG (SEQ ID NO: 12); and
(l) the pentapeptide Xaa-Pro-Gly-Val-Gly, or XPGVG (SEQ ID NO:13) where X is any natural or non-natural amino acid residue, and where X optionally varies among polymeric or oligomeric repeats.

The multipeptide structural units as defined in SEQ ID NOs: 1-13 form the elastin-like peptide component. In some embodiments, the ELP includes more than one structural unit. In some embodiments, the ELP includes two or more structural units of any of SEQ ID NOs: 1-13, which may be in any combination. In some embodiments, the two or more structural units are the same and are repeated tandemly. In some embodiments, the two or more structural units are different and are repeated alternately. In some embodiments, the ELP includes structural units repeated tandemly for one or more portions of sequence, and also different structural units repeated alternately for other portions of the sequence. In some embodiments, the ELP component is formed entirely (or almost entirely) of one or a combination of (e.g., 2, 3 or 4) structural units selected from SEQ ID NOS: 1-13. In other embodiments, at least 75%, or at least 80%, or at least 90% of the ELP component is formed from one or a combination of structural units selected from SEQ ID NOS: 1-13. In certain embodiments, the ELP contains repeat units, including tandem repeating units, of Val-Pro-Gly-X-Gly (SEQ ID NO: 3), where X is as defined above, and where the percentage of Val-Pro-Gly-X-Gly (SEQ ID NO: 3) units taken with respect to the entire ELP component (which may comprise structural units other than VPGXG) is greater than about 50%, or greater than about 75%, or greater than about 85%, or greater than about 95% of the ELP. The ELP may contain motifs of 5 to 15 structural units (e.g. about 10 structural units) of SEQ ID NO: 3, with the guest residue X varying among at least 2 or at least 3 of the units in the motif. The guest residues may be independently selected, such as from non-polar or hydrophobic residues, such as the amino acids V, I, L, A, G, and W (and may be selected so as to retain a desired inverse phase transition property). In certain embodiments, the guest residues are selected from V, G, and A. In some embodiments, the ELP includes the ELP 1 series (VPGXG: V5A2G3). In some embodiments, the ELP includes the ELP 4 series (VPGXG: V-5). In some embodiments, the ELP includes a combination of the ELP1 and ELP4 series. Without being bound by theory, the differences in the ELP polymer hydrophobicity is determined by the guest residues and their ratios, with the ELP 4 series being more hydrophobic than the ELP1 series.

In certain embodiments, the ELP contains repeat units, including tandem repeating units, of Xaa-Pro-Gly-Val-Gly (SEQ ID NO: 13), where X is as defined above, and where the percentage of Xaa-Pro-Gly-Val-Gly (SEQ ID NO: 13), units taken with respect to the entire ELP component (which may include structural units other than XPGVG) is greater than about 50%, or greater than about 75%, or greater than about 85%, or greater than about 95% of the ELP. The ELP may contain motifs of 5 to 15 structural units (e.g. about 9 structural units) of SEQ ID NO: 13, with the guest residue X varying among at least 2 or at least 3 of the units in the motif. The guest residues may be independently selected, such as from non-polar or hydrophobic residues, such as the amino acids V, I, L, A, G, and W (and may be selected so as to retain a desired inverse phase transition property). In certain embodiments, the guest residues are selected from V and A.

In certain embodiments, the ELP contains repeat units, including tandem repeating units of any of SEQ ID NOs: 1-13 either alone or in combination. In one embodiment, the ELP contains repeats of two or more of any of SEQ ID NOs: 1-13 in combination. In certain embodiments, the ELP contains repeats of SEQ ID NO: 3 and SEQ ID NO: 13. In some embodiments, the ELP contains repeats of SEQ ID NO: 3 and SEQ ID NO: 13, wherein the guest residues are independently selected, such as from non-polar or hydrophobic residues, such as the amino acids V, I, L, A, G, and W (and may be selected so as to retain a desired inverse phase transition property). In certain embodiments, the guest residues are selected from V and A. In some embodiments, the ELP comprises 9mers comprising five copies of a pentapeptide disclosed herein. In some embodiments, the ELP comprises 9mers comprising SEQ ID NOs: 3 and 13 in any combination. In some embodiments, the ELP comprises a sequence alternating between SEQ ID NOs: 3 and 13.

In some embodiments, the ELP may form a β-turn structure. Exemplary peptide sequences suitable for creating a β-turn structure are described in International Patent Application PCT/US96/05186. For example, the fourth residue (X) in the sequence VPGXG (SEQ ID NO: 3), can be altered without eliminating the formation of a β-turn.

The structure of exemplary ELPs may be described using the notation ELPk [XiYj-n], where k designates a particular ELP repeat unit, the bracketed capital letters are single letter amino acid codes and their corresponding subscripts designate the relative ratio of each guest residue X in the structural units (where applicable), and n describes the total length of the ELP in number of the structural repeats. For example, ELP1 [$V_5A_2G_3$-10] designates an ELP component containing 10 repeating units of the pentapeptide VPGXG (SEQ ID NO: 3), where X is valine, alanine, and glycine at a relative ratio of about 5:2:3; ELP1 [$K_1V_2F_1$-4] designates an ELP component containing 4 repeating units of the pentapeptide VPGXG (SEQ ID NO: 3), where X is lysine, valine, and phenylalanine at a relative ratio of about 1:2:1; ELP1 [$K_1V_7F_1$-9] designates a polypeptide containing 9 repeating units of the pentapeptide VPGXG (SEQ ID NO: 3), where X is lysine, valine, and phenylalanine at a relative ratio of about 1:7:1; ELP1 [V-5] designates a polypeptide containing 5 repeating units of the pentapeptide VPGXG (SEQ ID NO: 3), where X is valine; ELP1 [V-20] designates a polypeptide containing 20 repeating units of the pentapeptide VPGXG (SEQ ID NO: 3), where X is valine; ELP2 [5] designates a polypeptide containing 5 repeating units of the pentapeptide AVGVP (SEQ ID NO: 4); ELP3 [V-5] designates a polypeptide containing 5 repeating units of the pentapeptide IPGXG (SEQ ID NO: 5), where X is valine; ELP4 [V-5] designates a polypeptide containing 5 repeating units of the pentapeptide LPGXG (SEQ ID NO: 7), where X is valine.

With respect to ELP, the it is a function of the hydrophobicity of the guest residue. Thus, by varying the identity of the guest residue(s) and their mole fraction(s), ELPs can be synthesized that exhibit an inverse transition over a broad range. Thus, the it at a given ELP length may be decreased by incorporating a larger fraction of hydrophobic guest residues in the ELP sequence. Examples of suitable hydrophobic guest residues include valine, leucine, isoleucine, phenylalanine, tryptophan and methionine. Tyrosine, which is moderately hydrophobic, may also be used. Conversely, the Tt may be increased by incorporating residues, such as those selected from: glutamic acid, cysteine, lysine, aspartate, alanine, asparagine, serine, threonine, glycine, arginine, and glutamine.

For polypeptides having a molecular weight>100,000 Da, the hydrophobicity scale disclosed in PCT/US96/05186 provides one means for predicting the approximate it of a specific ELP sequence. For polypeptides having a molecular weight<100,000 Da, the it may be predicted or determined by the following quadratic function: Tt=M0+M1X+M2X2 where X is the MW of the fusion protein, and M0=116.21; M1=−1.7499; M2=0.010349.

The ELP in some embodiments is selected or designed to provide a Tt ranging from about 10 to about 37° C. at formulation conditions, such as from about 20 to about 37° C., or from about 25 to about 37° C. In some embodiments, the transition temperature at physiological conditions (e.g., 0.9% saline) is from about 34 to 36° C. to take into account a slightly lower peripheral temperature.

In certain embodiments, the amino acid sequence capable of forming the hydrogen-bonded matrix at body temperature is the ELP-1 series which includes [VPGXG (SEQ ID NO: 3)$]_m$, where m is any number from 1 to 200, each X is selected from V, G, and A, and wherein the ratio of V:G:A may be about 5:3:2. In certain embodiments, the amino acid sequence capable of forming the hydrogen-bonded matrix at body temperature includes [VPGXG (SEQ ID NO: 3)$]_{90}$, where each X is selected from V, G, and A, and wherein the ratio of V:G:A may be about 5:3:2. In certain embodiments, the amino acid sequence capable of forming the hydrogen-bonded matrix at body temperature includes [VPGXG (SEQ ID NO: 3)$]_{120}$, where each X is selected from V, G, and A, and wherein the ratio of V:G:A may be about 5:3:2.

In certain embodiments, the amino acid sequence capable of forming the hydrogen-bonded matrix at body temperature includes [VPGXG (SEQ ID NO: 3)$]_{144}$, where each X is selected from V, G, and A, and wherein the ratio of V:G:A is about 7:2:0. In certain embodiments, the amino acid sequence capable of forming the hydrogen-bonded matrix at body temperature includes [VPGXG (SEQ ID NO: 3)$]_{144}$, where each X is selected from V, G, and A, and wherein the ratio of V:G:A is about 7:0:2. In certain embodiments, the amino acid sequence capable of forming the hydrogen-bonded matrix at body temperature includes [VPGXG (SEQ ID NO: 3)$]_{144}$, where each X is selected from V, G, and A, and wherein the ratio of V:G:A is about 6:0:3. In certain embodiments, the amino acid sequence capable of forming the hydrogen-bonded matrix at body temperature includes [VPGXG (SEQ ID NO: 3)$]_{144}$, where each X is selected from V, G, and A, and wherein the ratio of V:G:A is about 5:2:2.

In certain embodiments, the amino acid sequence capable of forming the hydrogen-bonded matrix at body temperature includes [XPGVG (SEQ ID NO: 3)$]_m$, where m is any number from 1 to 200, each X is selected from V, G, and A. In certain embodiments, the amino acid sequence capable of forming the hydrogen-bonded matrix at body temperature includes [XPGVG (SEQ ID NO: 3)$]_{144}$, where m is any number from 1 to 200, each X is selected from V, G, and A and wherein the ratio of V:G:A is about 5:0:4. In certain embodiments, the amino acid sequence capable of forming the hydrogen-bonded matrix at body temperature includes [XPGVG (SEQ ID NO: 3)$]_{144}$, where each X is selected from V, G, and A, and wherein the ratio of V:G:A is about 5:0:4.

Alternatively, the amino acid sequence capable of forming the matrix at body temperature is the ELP-4 series which includes [VPGVG (SEQ ID NO:3)$]_{90}$, or [VPGVG (SEQ ID NO:3)$]_{120}$. 120 structural units of this ELP can provide a transition temperature at about 37° C. with about 0.005 to about 0.05 mg/ml (e.g., about 0.01 mg/ml) of protein. Alternatively, the amino acid sequence capable of forming the matrix at body temperature includes [VPGXG (SEQ ID NO:3)$]_{144}$ or [XPGVG (SEQ ID NO:3)$]_{144}$. For example, 144 structural units of either of these ELPs can provide a transition temperature at between about 28° C. and 35° C.

Elastin-like-peptide (ELP) protein polymers and recombinant fusion proteins can be prepared as described in U.S. Patent Publication No. 2010/0022455. In some embodiments, the ELP protein polymers are constructed through recursive ligation to rapidly clone highly repetitive polypeptides of any sequence and specified length over a large range of molecular weights. In a single cycle, two halves of a parent plasmid, each containing a copy of an oligomer, are ligated together, thereby dimerizing the oligomer and reconstituting a functional plasmid. This process is carried out recursively to assemble an oligomeric gene with the desired number of repeats. For example, one ELP structural subunit (e.g. a pentapeptide or a 9mer of pentapeptides) is inserted into a vector. The vector is digested, and another ELP structural unit (e.g. a pentapeptide or a 9mer of pentapeptides) is inserted. Each subsequent round of digestion and ligation doubles the number of ELP structural units contained in the resulting vector until the ELP polymer is the desired length.

In other embodiments, the amino acid sequence capable of forming the matrix at body temperature includes a random coil or non-globular extended structure. For example, the amino acid sequence capable of forming the matrix at body temperature includes an amino acid sequence disclosed in U.S. Patent Publication No. 2008/0286808, WIPO Patent Publication No, 2008/155134, and U.S. Patent Publication No. 2011/0123487.

For example, in some embodiments the amino acid sequence includes an unstructured recombinant polymer of at least 40 amino acids. For example, the unstructured polymer may be defined where the sum of glycine (G), aspartate (D), alanine (A), serine (S), threonine (T), glutamate (E) and proline (P) residues contained in the unstructured polymer, constitutes more than about 80% of the total amino acids. In some embodiments, at least 50% of the amino acids are devoid of secondary structure as determined by the Chou-Fasman algorithm. The unstructured polymer includes more than about 100, 150, 200 or more contiguous amino acids. In some embodiments, the amino acid sequence forms a random coil domain. In particular, a polypeptide or amino acid polymer having or forming "random coil conformation" substantially lacks a defined secondary and tertiary structure.

In various embodiments, the intended subject is human, and the body temperature is about 37° C., and thus the therapeutic agent is designed to provide a sustained release at or near this temperature (e.g. between about 28° C. to about 37° C.). A slow release into the circulation with reversal of hydrogen bonding and/or hydrophobic interactions is driven by a drop in concentration as the product diffuses at the injection site, even though body temperature remains constant. In other embodiments, the subject is a non-human mammal, and the therapeutic agent is designed to exhibit a sustained release at the body temperature of the mammal, which may be from about 30 to about 40° C. in some embodiments, such as for certain domesticated pets (e.g., dog or cat) or livestock (e.g., cow, horse, sheep, or pig). Generally, the it is higher than the storage conditions of the formulation (which may be from about 2 to about 30° C., or about 10 to about 25° C., or from about 15 to about 22° C., or from about 2 to about 8° C.), such that the therapeutic agent remains in solution for injection. Alternatively, the therapeutic agent may be stored frozen, such as from about −80° C. to about −20° C.

Disorders Associated with CFTR Protein Dysfunction and Methods of Treatment

Dysfunction of the CFTR protein occurs in various diseases or disorders, including but not limited to Cystic Fibrosis, Chronic Obstructive Pulmonary Disease (COPD), exocrine organ disorders, non-Cystic Fibrosis bronchiectasis, recurrent pancreatitis, congenital bilateral absence of vas deferens and disorders associated with an acquired defect in CFTR protein function (e.g. caused by smoking or other environmental factors). In an exemplary embodiment, CFTR dysfunction is associated with Cystic Fibrosis. In another exemplary embodiment, CFTR dysfunction is associated with smoking-related lung damage.

As used herein, the term "CFTR protein dysfunction" refers to any decrease in CFTR protein function compared to a healthy subject. The CFTR protein may exhibit a total loss of function, or it may exhibit some residual or partial function compared to CFTR function in a healthy subject. In some embodiments, CFTR function is decreased by about 1%, about 5%, about 10%, about 20%, about 30%, about 40%, about 50%, about 60%, about 70%, about 80%, about 90%, about 95%, or about 99% compared with CFTR protein function in a healthy subject.

In some embodiments, CFTR protein dysfunction is characterized by a loss of chloride ion transport across the cell membrane. In some embodiments, CFTR protein dysfunction is characterized by a decrease in water transport across the cell membrane. In some embodiments, the CFTR protein is mis-localized in the cell. In some embodiments, the CFTR protein is not localized to the apical membrane of the cell.

CFTR protein dysfunction symptoms vary among individual patients, but in general, CFTR protein dysfunction is characterized by production of thick mucus that for example, clogs respiratory airways, obstructs the intestines, blocks pancreatic and bile ducts, interferes with liver function, and damages tissue. The tissue damage observed in subjects with CFTR protein dysfunction may affect a variety of tissues and organs including, but not limited to, the lungs, the pancreas, the liver, the intestines, the reproductive system, the airway system, and/or the digestive system.

In some embodiments, CFTR protein dysfunction is characterized by an increased salinity in sweat or other body fluids. In some embodiments, CFTR protein dysfunction is characterized by defective excretion of bicarbonate in the gut. In some embodiments, CFTR protein dysfunction is characterized by increased incidence of infections, including but not limited to infections of the airway. In some embodiments, CFTR protein dysfunction is characterized by an inflammatory lung phenotype. In some embodiments, CFTR protein dysfunction is characterized by impaired respiratory activity. In some embodiments, CFTR protein dysfunction is characterized by chronic digestive problems. In some embodiments, Cystic Fibrosis is characterized by male infertility. A patient will not necessarily present with all of these symptoms, some of which might be absent in milder cases of CFTR protein dysfunction, or earlier during disease progression.

In some aspects, the present disclosure provides a method of treating, delaying, or ameliorating symptoms of CFTR protein dysfunction comprising administering pharmaceutical compositions of a vasoactive intestinal peptide and one or more ELPs to a subject in need.

Cystic Fibrosis caused by any one or more mutations in the CFTR gene may be treated, delayed, or ameliorated by the pharmaceutical compositions disclosed herein. In some embodiments, the subject is homozygous for one or more mutations in the CFTR gene. In some embodiments, the subject is heterozygous for one or more mutations in the CFTR gene. In some embodiments, the one or more mutations are nonsense mutations. In some embodiments, the one or more mutations are gating mutations. In some embodiments, the one or more mutations are protein processing mutations. In some embodiments, the one or more mutations are conductance mutations. In some embodiments, the one or more mutations are translation mutations. Examples of CFTR mutations include, but are not limited to, F508del, G542X, G85E, R334W, Y122X, G551D, R117H, A455E, S549R, R553X, V520F, R1162X, R347H, N1203K, S549N, R347P, R5601, S1255X, Add9T, Y1092X, M1191K, W1282X, 3659de;C, 394delTT, 3905insT, 1078delT, delta I507, 3876delA, 2184delA, 2307insA, 711+1G>T, 1717-1G>A, 2789+5G>A, 1898+5G>T, 3120+1G>A, 621+1G>T, 3849+10kbC>T, 1898+1G>A, 2183 AA>G, and/or 5/7/9T. In a preferred embodiment, the mutation is F508del.

In some embodiments, the CFTR protein dysfunction is acquired (e.g. through smoking or by exposure to environmental damage). In some embodiments, the CFTR protein dysfunction is not associated with a mutation in the CFTR gene.

The treatment, delay, or amelioration of CFTR protein dysfunction symptoms may be measured by any means known in the art. For example, tests used to evaluate patients with CFTR protein dysfunction include, but are not limited to, a sweat chloride test, an immunoreactive trypsinogen test (IRT), a blood test (e.g. to test pancreatic function), chest X-rays, lung function tests, a nasal potential difference test, CFTR protein function assays (e.g. testing the efflux of ions in the cells), cellular current measurement test, forced expiratory volume in 1 second (FEV1), and/or immunofluorescence to detect the localization of the CFTR protein in the cell.

The effects of administration of the pharmaceutical compositions disclosed herein may be measured in any relevant tissue and/or organ, including but not limited to epithelial cells (e.g. nasal epithelial cells), lungs, pancreas, the digestive system, the reproductive system and/or the airway system.

In some embodiments, administration of the pharmaceutical compositions disclosed herein prevents, delays, or ameliorates one or more CFTR protein dysfunction symptoms in a subject. In some embodiments, one or more CFTR protein dysfunction symptoms are prevented, delayed, or ameliorated for about 1 week, about 1 month, about 2 months, about 3 months, about 4 months, about 5 months, about 6 months, about 8 months, about 1 year, about 2 years, about 5 years, and/or about 10 years compared with the one or more CFTR protein dysfunction symptoms in an untreated subject with CFTR dysfunction. In some embodiments, one or more CFTR protein dysfunction symptoms are prevented, delayed, or ameliorated by about 1%, about 5%, about 10%, about 20%, about 30%, about 40%, about 50%, about 60%, about 70%, about 80%, about 90%, about 95%, or about 99% compared with the one or more CFTR protein dysfunction symptoms in an untreated subject with CFTR dysfunction. In some embodiments, this prevention, delay, or amelioration of one or more CFTR protein dysfunction symptoms is observed at the time points disclosed herein.

In some embodiments, administration of the pharmaceutical compositions disclosed herein decrease sweat chloride levels in a subject compared to an untreated subject with CFTR protein dysfunction. In some embodiments, sweat chloride levels are decreased for about 1 week, about 1 month, about 2 months, about 3 months, about 4 months, about 5 months, about 6 months, about 8 months, about 1 year, about 2 years, about 5 years, and/or about 10 years compared with the mucus viscosity of an untreated subject with CFTR protein dysfunction, in some embodiments, sweat chloride levels are decreased by about 1%, about 5%, about 10%, about 20%, about 30%, about 40%, about 50%, about 60%, about 70%, about 80%, about 90%, about 95%, or about 99% compared with the mucus viscosity of an untreated subject with CFTR protein dysfunction. In some embodiments, this decrease in sweat chloride levels is observed at the time points disclosed herein.

In some embodiments, administration of the pharmaceutical compositions disclosed herein improves mucus viscosity in a subject compared to an untreated subject with CFTR protein dysfunction. In some embodiments, mucus viscosity is improved for about 1 week, about 1 month, about 2 months, about 3 months, about 4 months, about 5 months, about 6 months, about 8 months, about 1 year, about 2 years, about 5 years, and/or about 10 years compared with the mucus viscosity of an untreated subject with CFTR protein dysfunction. In some embodiments, mucus viscosity is improved by about 1%, about 5%, about 10%, about 20%, about 30%, about 40%, about 50%, about 60%, about 70%, about 80%, about 90%, about 95%, or about 99% compared with the mucus viscosity of an untreated subject with CFTR protein dysfunction. In some embodiments, this improvement in mucus viscosity is observed at the time points disclosed herein.

In some embodiments, administration of the pharmaceutical compositions disclosed herein prevents, delays, or ameliorates the development of fibrosis in a subject. In some embodiments, development of fibrosis is prevented, delayed, or ameliorated for about 1 week, about 1 month, about 2 months, about 3 months, about 4 months, about 5 months, about 6 months, about 8 months, about 1 year, about 2 years, about 5 years, and/or about 10 years compared with the development of fibrosis in an untreated subject with CFTR protein dysfunction. In some embodiments, the development of fibrosis is prevented, delayed, or ameliorated by about 1%, about 5%, about 10%, about 20%, about 30%, about 40%, about 50%, about 60%, about 70%, about 80%, about 90%, about 95%, or about 99% compared with the development of fibrosis in an untreated subject with CFTR protein dysfunction. In some embodiments, this prevention, delay, or amelioration of fibrosis is observed at the time points disclosed herein.

In some embodiments, administration of the pharmaceutical compositions disclosed herein prevents, delays, or ameliorates tissue damage in one or more organs and/or tissues in a subject. In some embodiments, the tissue damage is caused by inflammation. In preferred embodiments, administration of the pharmaceutical compositions disclosed herein prevents, delays, or ameliorates tissue damage in the digestive tract. In some embodiments, preventing, delaying, or ameliorating tissue damage in the digestive tract alleviates digestive problems in the subject. In preferred embodiments, administration of the pharmaceutical compositions disclosed herein prevents, delays, or ameliorates tissue damage in the lungs in a subject. In some embodiments, tissue damage is prevented, delayed, or ameliorated for about 1 week, about 1 month, about 2 months, about 3 months, about 4 months, about 5 months, about 6 months, about 8 months, about 1 year, about 2 years, about 5 years, or about 10 years compared with the tissue damage in an untreated subject with CFTR protein dysfunction. In some embodiments, tissue damage is prevented, delayed, or ameliorated by about 1%, about 5%, about 10%, about 20%, about 30%, about 40%, about 50%, about 60%, about 70%, about 80%, about 90%, about 95%, or about 99% compared with the tissue damage in an untreated subject with CFTR protein dysfunction. In some embodiments, this prevention, delay, or amelioration of tissue damage is observed at the time points disclosed herein.

In some embodiments, administration of the pharmaceutical compositions disclosed herein improves respiratory function in a subject. In some embodiments the improvement in respiratory function is determined by measuring the forced expiratory volume in 1 second (FEV1) using methods well known in the art. In some embodiments, respiratory function is improved by about 20%, about 30%, about 40%, about 50%, about 60%, about 70%, about 80%, about 90%, about 95%, or about 99% of the respiratory function of an untreated subject with CFTR protein dysfunction. In some embodiments, administration of the pharmaceutical compositions disclosed herein improves respiratory function in a subject for about 1 week, about 1 month, about 2 months, about 3 months, about 4 months, about 5 months, about 6 months, about 8 months, about 1 year, about 2 years, about 5 years, and/or about 10 years compared to the respiratory function of an untreated subject with CFTR protein dysfunction. In some embodiments, the respiratory function is improved in the subject at the time points disclosed herein.

In some embodiments, administration of the pharmaceutical compositions disclosed herein improves water transport across cell membranes in a subject. In some embodiments, the water transport is improved by about 20%, about 30%, about 40%, about 50%, about 60%, about 70%, about 80%, about 90%, about 95%, or about 99% of the rate of water transport of an untreated subject with CFTR protein dysfunction. In some embodiments, administration of the pharmaceutical compositions disclosed herein improves water transport across cell membranes in a subject for about 1 week, about 1 month, about 2 months, about 3 months, about 4 months, about 5 months, about 6 months, about 8 months, about 1 year, about 2 years, about 5 years, and/or about 10 years compared to the rate of water transport of an untreated subject with CFTR protein dysfunction. In some embodiments, the rate of water transport across cell membranes is improved in the subject at the time points disclosed herein.

In some embodiments, administration of the pharmaceutical compositions disclosed herein increases CFTR protein function in a subject. In some embodiments, the CFTR protein function is the transport of chloride ions across the cell membrane. In some embodiments, administration of the pharmaceutical compositions disclosed herein increases CFTR protein function by about 20%, about 30%, about 40%, about 50%, about 60%, about 70%, about 80%, about 90%, about 95%, or about 99% compared with the (Yip, protein function in an untreated subject with CFTR protein dysfunction. In some embodiments, administration of the pharmaceutical compositions disclosed herein increases CFTR protein function in a subject for about 1 week, about 1 month, about 2 months, about 3 months, about 4 months, about 5 months, about 6 months, about 8 months, about 1 year, about 2 years, about 5 years, and/or about 10 years compared with CFTR protein function in an untreated subject with CFTR protein dysfunction. In some embodiments, the degree of increased CFTR protein function is observed in the subject at the time points disclosed herein.

In some embodiments, administration of the pharmaceutical compositions disclosed herein increases CFTR protein function more than other CFTR protein dysfunction treatments. In some embodiments, the CFTR protein function is the transport of chloride ions across the cell membrane. In some embodiments, the other CFTR protein dysfunction treatments are CFTR correctors, CFTR potentiators, and/or nonsense mutation suppressors (e.g. ataluren). In some embodiments, the other Cystic Fibrosis treatment is a combination treatment. In some embodiments, the combination treatment is a combination of a CFTR corrector and a CFTR potentiator. In some embodiments, the other CFTR protein dysfunction treatments are VX770, VX809, or VX661. In some embodiments, administration of the pharmaceutical compositions disclosed herein increases CFTR protein function by about 20%, about 30%, about 40%, about 50%, about 60%, about 70%, about 80%, about 90%, about 95%, or about 99% compared with the CFTR protein function in a CFTR protein dysfunction subject treated with the other CFTR protein dysfunction treatment. In some embodiments, administration of the pharmaceutical compositions disclosed herein increases CFTR protein function in a subject for about 1 week, about 1 month, about 2 months, about 3 months, about 4 months, about 5 months, about 6 months, about 8 months, about 1 year, about 2 years, about 5 years, and/or about 10 years compared with the CFTR protein function in a subject with CFTR protein dysfunction treated with the other CFTR protein dysfunction treatment. In some embodiments, the degree of increased CFTR protein function is observed in the subject at the time points disclosed herein.

In some embodiments, administration of the pharmaceutical compositions disclosed herein increases the density of the CFTR protein at the apical cell membrane in a subject. In some embodiments, administration of the pharmaceutical compositions disclosed herein increases the density of the CFTR protein at the apical cell membrane in a subject as measured by immunoblotting. In some embodiments, the CFTR protein is not recycled as quickly as in an untreated subject with CFTR protein dysfunction. In some embodiments, administration of the pharmaceutical compositions disclosed herein increases the density of the CFTR protein at the apical cell membrane by about 20%, about 30%, about 40%, about 50%, about 60%, about 70%, about 80%, about 90%, about 95%, or about 99% compared to the density of the CFTR protein at the apical cell membrane in an untreated subject with CFTR protein dysfunction. In some embodiments, administration of the pharmaceutical compositions disclosed herein increases the density of the CFTR protein at the apical cell membrane in a subject for about 1 week, about 1 month, about 2 months, about 3 months, about 4 months, about 5 months, about 6 months, about 8 months, about 1 year, about 2 years, about 5 years, and/or about 10 years compared with the density of the CFTR protein at the apical cell membrane in an untreated subject with CFTR protein dysfunction. In some embodiments, the degree of increased localization of the CFTR protein in the cell membrane is observed in the subject at the time points disclosed herein.

In some embodiments, administration of the pharmaceutical compositions disclosed herein corrects CFTR protein maturation and membrane expression in a subject. In some embodiments, this correction of CFTR protein maturation and membrane expression is measured by immunoblotting or immunostaining with molecules that bind to CFTR. In some embodiments, administration of the pharmaceutical compositions disclosed herein increases the CFTR immunoblot or immunostain signal by about 20%, about 30%, about 40%, about 50%, about 60%, about 70%, about 80%, about 90%, about 95%, or about 99% compared to the CFTR immunoblot or immunostain signal in an untreated subject with CFTR protein dysfunction. In some embodiments, administration of the pharmaceutical compositions disclosed herein increases the CFTR immunoblot or immunostain signal for about 1 week, about 1 month, about 2 months, about 3 months, about 4 months, about 5 months, about 6 months, about 8 months, about 1 year, about 2 years, about 5 years, and/or about 10 years compared with the CFTR immunoblot or immunostain signal in an untreated subject with CFTR protein dysfunction. In some embodiments, the degree of increased CFTR immunoblot or immunostain signal is observed in the subject at the time points disclosed herein.

Pharmaceutical Compositions and Administration

The present disclosure provides pharmaceutical compositions including a Vasoactive Intestinal Peptide and one or more ELPs with one or more pharmaceutically acceptable excipients and/or diluents. For example, such excipients include salts, and other excipients that may act to stabilize hydrogen bonding. Exemplary salts include alkaline earth metal salts such as sodium, potassium, and calcium. Counter ions include chloride and phosphate. Exemplary salts include sodium chloride, potassium chloride, magnesium chloride, calcium chloride, and potassium phosphate.

The protein concentration in the formulation is tailored to drive the formation of the matrix at the temperature of administration. For example, higher protein concentrations help drive the formation of the matrix, and the protein concentration needed for this purpose varies depending on the ELP series used. For example, in embodiments using an ELP1-120, or amino acid sequences with comparable transition temperatures, the protein is present in the range of about 1 mg/mL to about 200 mg/mL, or is present in the range of about 5 mg/mL to about 125 mg/mL. The vasoactive intestinal peptide portion of the fusion protein in the therapeutic composition may be present in the range of about 10 mg/mL to about 50 mg/mL, or about 15 mg/mL to about 30 mg/mL, or about 10-20 mg/ml, or about 5-15 trig/ml, or about 1-10 mg/mi. In embodiments using an ELP4-120, or amino acid sequences with comparable transition temperatures, the protein is present in the range of about 0.005 mg/mL to about 10 mg/mL, or is present in the range of about 0.01 mg/mL, to about 5 mg/mL. In some embodiments, the vasoactive intestinal peptide is present in the range of about 0.5 mg/mL, to about 200 mg/mL, or is present in the range of about 5 mg/mL, to about 125 mg/mL. In some embodiments, vasoactive intestinal peptide is present in the range of about 10 mg/mL, to about 50 mg/mL, or the range of about 15 mg/mL to about 30 mg/mL.

The pharmaceutical composition is generally prepared such that it does not form the matrix at storage conditions. Storage conditions are generally less than the transition temperature of the formulation, such as less than about 32° C., or less than about 30° C., or less than about 27° C., or less than about 25° C., or less than about 20° C., or less than about 15° C., or less than about 10° C. The storage condition may, alternatively, be below freezing, such as less than about −10° C., or less than about −20° C., or less than about −40° C., or less than about −70° C. For example, the formulation may be isotonic with blood or have an ionic strength that mimics physiological conditions. For example, the formulation may have an ionic strength of at least that of 25 mM Sodium Chloride, or at least that of 30 mM Sodium chloride, or at least that of 40 mM Sodium Chloride, or at least that of 50 mM Sodium Chloride, or at least that of 75 mM Sodium Chloride, or at least that of 100 mM Sodium Chloride, or at least that of 150 mM Sodium Chloride. In certain embodiments, the formulation has an ionic strength less than that of 0.9% saline. In some embodiments, the pharmaceutical composition includes two or more of calcium chloride, magnesium chloride, potassium chloride, potassium dihydrogen phosphate, potassium hydrogen phosphate, sodium chloride, sodium dihydrogen phosphate and disodium hydrogen phosphate. The liquid pharmaceutical composition can be stored frozen, refrigerated or at room temperature.

In exemplary embodiments, the disclosure provides a sustained release pharmaceutical composition that includes a vasoactive intestinal peptide or derivatives thereof (e.g. having an N-terminal moiety such as a Methionine) and one or more amino acid sequences including [VPGXG (SEQ ID NO:3)]$_{90}$, or [VPGXG (SEQ ID NO:3)]$_{120}$, where each X is selected from V, G, and A. V, G, and A may be present at a ratio of about 5:3:2, of about 7:2:0, of about 7:0:2, of about 6:0:3, or of about 5:2:2. Alternatively, the amino acid sequence includes [VPGVG (SEQ ID NO:3)]$_{90}$ or [VPGVG (SEQ ID NO:3)]$_{120}$. In exemplary embodiments, the disclosure provides a sustained release pharmaceutical composition that includes a vasoactive intestinal peptide or derivatives thereof (e.g. having an N-terminal moiety such as a Methionine) and one or more amino acid sequences including [XPGVG (SEQ ID NO:3)]$_{144}$, where each X is selected from V, G, and A. V, G, and A may be present at a ratio of about 5:0:4. Alternatively, the amino acid sequence includes [XPGVG (SEQ ID NO:3)]$_{144}$. The formulation further includes one or more pharmaceutically acceptable excipients and/or diluents for formation of a reversible matrix from an aqueous form upon administration to a human subject. VIP and derivatives thereof are disclosed in U.S. Patent Publication No. 2011/0178017.

Other formulation components for achieving the desired stability, fix example, may also be employed. Such components include one or more amino acids or sugar alcohol (e.g., mannitol), surfactants (e.g. polysorbate 20, polysorbate 80), preservatives, and buffering agents (e.g. histidine), and such ingredients are well known in the art. In certain embodiments, the pharmaceutical compositions disclosed herein have enhanced efficacy, bioavailability, therapeutic half-life, persistence, degradation assistance, etc.

Advantageously, the compositions provide for prolonged pharmacokinetic exposure due to sustained release of the active agent. In particular aspects, the maximal exposure level may be achieved at about 10 hours, about 24 hours, about 48 hours or about 72 hours after administration; typically the maximum exposure rate is achieved between about 10 hours and about 48 hours after administration. After the maximal exposure rate is achieved the compositions may achieve a sustained rate of release whereby a substantial percentage of the maximal rate is obtained for a period of time. For example, the sustained rate may about 50%, about 60%, about 70%, about 80%, about 90% or about 100%. Exemplary periods of time for maintaining the sustained rate are about 3 days, about 4 days, about 5 days, about 6 days, about 1 week, about 2 weeks, about 4 weeks, about 6 weeks, or about 8 weeks, after the maximal exposure rate is achieved. Subsequently, the sustained rate may lower to a reduced exposure rate. Such reduced exposure rates may be about 5%, about 10%, about 20%, about 30%, about 40%, about 50% or about 60%.

In various embodiments, the plasma concentration of the active agent does not change by more than a factor of 10, or a factor of about 5, or a factor of about 3 over the course of a plurality of administrations, such as at least 2, at least about 5, or at least about 10 administrations of the formulation. The administrations are substantially evenly spaced, such as, for example, about daily, or about once per week, or from one to about five times per month, or about once every two months, or about once every three months.

In another aspect, the disclosure provides a method for delivering a sustained release regimen of a vasoactive intestinal peptide or analogues thereof. The method comprises administering the pharmaceutical composition described herein to a subject in need, wherein the pharmaceutical composition is administered from about 1 to about 8 times per month. In some embodiments, the pharmaceutical composition is administered about 1 time, about 2 times, about 3 times, and/or about 4 times per month. In some embodiments, the pharmaceutical composition is administered weekly. In some embodiments, the pharmaceutical composition is administered daily. In some embodiments, the pharmaceutical composition is administered from one to three times weekly. In some embodiments, the pharmaceutical composition is administered once every two weeks. In some embodiments, the pharmaceutical composition is administered from one to two times a month. In particular embodiments, the pharmaceutical composition is administered about 1 time per month. In some embodiments, the pharmaceutical composition is administered about once every 2 months, about once every 3 months, about once every 4 months, about once every 5 months, and/or about once every 6 months. In some embodiments, VIP may have an additional moiety such as Methionine at the N-terminus to alter the receptor binding profile, as described in U.S. Patent Publication No. 2011/0178017. In some embodiments, VIP is fused to ELP1 (having from about 90 to about 150 ELP units). In some embodiments, VIP is fused to ELP4 (having from about (having from about 90 to about 150 ELP units). The pharmaceutical composition can be packaged in the form of pre-filled pens or syringes for administration once per week, twice per week, or from one to eight times per month, or alternatively filled in conventional vials and the like.

In some embodiments, the pharmaceutical compositions disclosed herein are administered chronically. In some embodiments, the pharmaceutical compositions disclosed herein are administered for about 6 months, for about 7 months, for about 8 months, for about 9 months, for about 10 months, for about 11 months, for about 1 year, for about 2 years, for about 3 years, for about 4 years, for about 5 years, for about 10 years or more. The pharmaceutical compositions may be administered at any required dose and/or frequency disclosed herein.

In some embodiments, the pharmaceutical compositions disclosed herein are administered until CFTR protein dysfunction symptoms improve. In some embodiments, the pharmaceutical compositions disclosed herein are administered until CFTR protein dysfunction symptoms are ameliorated, delayed, and/or cured.

In some embodiments, the pharmaceutical compositions disclosed herein are administered before the patient begins to exhibit one or more CFTR protein dysfunction symptoms. In some embodiments, the pharmaceutical compositions disclosed herein are administered immediately or shortly after diagnosis. In some embodiments, the pharmaceutical compositions disclosed herein are administered at the onset of CFTR protein dysfunction symptoms. In some embodiments, the pharmaceutical compositions disclosed herein are administered at the onset of an exacerbation of CFTR protein dysfunction symptoms.

The therapeutic agent is generally for "systemic delivery," meaning that the agent is not delivered locally to a pathological site or a site of action. Instead, the agent is absorbed into the bloodstream from the injection site, where the agent acts systemically or is transported to a site of action via the circulation. The therapeutic agent may be administered by any known route, such as for example, orally, intravenously, intramuscularly, nasally, subcutaneously, intra-vaginally, and intra-rectally. In one embodiment, the formulation is generally for subcutaneous administration. In one embodiment, the pharmacokinetic (PK) parameters are prolonged when the agent is administered subcutaneously. In one embodiment, the half-life of the fusion protein is prolonged. In one embodiment, the PK parameters when the agent is administered subcutaneously are prolonged compared with the agent administered by other means (e.g. intravenously). In one embodiment, the depot of the agent is prolonged when the agent is administered subcutaneously compared with the agent administered by other means (e.g. intravenously).

In some embodiments, the formulation is administered about monthly, and may be administered subcutaneously or intramuscularly. In some embodiments, the formulation is administered about weekly, and may be administered subcutaneously or intramuscularly. In some embodiments, the site of administration is not a pathological site, for example, is not the intended site of action.

The pharmaceutical compositions disclosed herein may be administered in smaller doses and/or less frequently than unfused or unconjugated counterparts. While one of skill in the art can determine the desirable dose in each case, a suitable dose of the therapeutic agent for achievement of therapeutic benefit, may, for example, be in a range of about 1 microgram (μg) to about 100 milligrams (mg) per kilogram body weight of the recipient per day, preferably in a range of about 10 μg to about 50 mg per kilogram body weight per day and most preferably in a range of about 10 μg to about 50 mg per kilogram body weight per day. In some embodiments, the pharmaceutical composition is administered at a low dose. In some embodiments, the pharmaceutical composition is administered at a dose between 1 mg per kilogram per body weight per day to about 9 mg per kilogram per body weight per day. In some embodiments, the pharmaceutical composition is administered at about 1 mg per kilogram body weight per day, about 3 mg per kilogram body weight per day, and/or about 9 mg per kilogram body weight per day. The desired dose may be presented as one dose or two or more sub-doses administered at appropriate intervals throughout the day. These sub-doses can be administered in unit dosage forms, for example, containing from about 10 μg to about 1000 mg, preferably from about 50 μg to about 500 mg, and most preferably from about 50 μg to about 250 mg of active ingredient per unit dosage form. Alternatively, if the condition of the recipient so requires, the doses may be administered as a continuous infusion.

In certain embodiments, the subject is a human, but in other embodiments may be a non-human mammal, such as a domesticated pet dog or cat), or livestock or farm animal (e.g., horse, cow, sheep, or pig).

Combination Therapies

The pharmaceutical compositions disclosed herein may be administered with various therapies used to treat, prevent, delay, or ameliorate symptoms of CFTR protein dysfunction, including, but not limited to, physical therapy, oxygen therapy, respiratory therapy, gene therapy, bronchial or postural drainage, and/or therapeutic agents. The pharmaceutical compositions disclosed herein may be used alone or in combination with one or more therapeutic agents. The one or more therapeutic agents may be any compound, molecule, or substance that exerts therapeutic effect to a subject in need thereof.

The one or more therapeutic agents May be "co-administered", i.e., administered together in a coordinated fashion to a subject, either as separate pharmaceutical compositions or admixed in a single pharmaceutical composition. By "co-administered", the one or more therapeutic agents may also be administered simultaneously with the present pharmaceutical compositions, or be administered separately, including at different times and with different frequencies. The one or more therapeutic agents may be administered by any known route, such as orally, intravenously, intramuscularly, nasally, subcutaneously, intra-vaginally, intra-rectally, and the like; and the therapeutic agent may also be administered by any conventional route. In many embodiments, at least one therapeutic agent may be administered subcutaneously.

These one or more therapeutic agents include, but are not limited to, antibiotics, mucolytics, CFTR potentiators (e.g. flavones, xanthines, benzimidazoles, ivacaftor (VX-770), QBW251, PG-01, VR-532), CFTR correctors (e.g. lumacaftor (VX-809), VX-661, curcumin, miglustat, sildenafil, 4-phenyl-butyrate, corr-4a, glafanine, RDR1), nonsense mutation read-through agents (e.g. ataluren), CFTR production correctors, read-through agents, small molecule ion channel agents, osmotic agents, RNA repair, soluble guanylate cyclase stimulators, S-nitrosoglutathione reductase inhibitors, DNase, antifungals, bronchodilators, nitric oxide, anticholinergics, nonsteroidal anti-inflammatory drugs (NSAIDs), membrane stabilizers, corticosteroids, enzyme replacement therapy, corticosteroids, glucocorticosteroids, decongestants and/or antifibrotic agents (e.g. halofuginone). In some embodiments, a CFTR potentiator and a CFTR corrector are co-administered. In some embodiments, the pharmaceutical compositions disclosed herein are co-administered with one or more CFTR potentiators and/or CFTR correctors. In preferred embodiments, the pharmaceutical compositions disclosed herein are co-administered with VX770, VX809, and/or VX661.

In some embodiments, the co-administration of the pharmaceutical compositions disclosed herein with one or more therapeutic agents has a synergistic effect. In some, embodiments, the synergistic effect is on CFTR protein function. In some embodiments, the one or more therapeutic agents are CFTR correctors. In some embodiments, the one or more therapeutic agents are CFTR potentiators. In some, embodiments, the one or more therapeutic agents are VX770, VX809, and/or VX661.

When two or more therapeutic agents are used in combination, the dosage of each therapeutic agent is commonly identical to the dosage of the agent when used independently. However, when a therapeutic agent interferes with the metabolism of others, the dosage of each therapeutic agent is properly adjusted. Alternatively, where the two or more therapeutic agents show synergistic effects, the dose of one or more may be reduced. Each therapeutic agent may be administered simultaneously or separately in an appropriate time interval.

It should be understood that singular forms such as "a," "an," and "the" are used throughout this application for convenience, however, except where context or an explicit statement indicates otherwise, the singular forms are intended to include the plural. All numerical ranges should be understood to include each and every numerical point within the numerical range, and should be interpreted as reciting each and every numerical point individually. The endpoints of all ranges directed to the same component or property are inclusive, and intended to be independently combinable.

The term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Unless defined otherwise, all technical and scientific, terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein.

This disclosure is further illustrated by the following non-limiting examples.

EXAMPLES

Example 1: Administration of PB1046 or PB1120 Rescues F508del-CFTR Function

Highly functional F508del-CFTR can be rescued in Cystic Fibrosis epithelial cells by correcting its misfolding to promote membrane targeting while increasing surface stability. While VIP has been shown to rescue this mutation in Cystic Fibrosis cells, the brief half-life of this protein in serum (≤1 minute) limits its therapeutic use. Disclosed herein are long lasting, stable VIP therapeutics, PB1120 and PB1046 which include ELP sequences. These data demonstrate PB1120 and PB1046 rescue F508del-CFTR.

A human nasal epithelial cell line JME/CF15, derived from a Cystic Fibrosis patient homozygous for the F508del mutation (Jefferson (1990)) was used to evaluate the effect of VIP compounds on CFTR protein function. Cells were cultured at 37° C. with at 5% $CO_2$— 95% humidity in DMEM-F12 with 10% FBS and supplemented with transferrin (5 μg/ml), triiodothyronine (2 nM), insulin (5 μg/ml), hydrocortisone (1.1 μM), EGF (1.64 nM), epinephrine (5.5 μM), and adenine (18 μM). Cells were maintained at 37° C. and incubated with 900 mM VIP, 1.2 μM PB1046 (SEQ ID NO: 15), or 1 μM PB1120 (SEQ ID NO: 20) for 18 or 24 hours before the assaying for iodide efflux. For comparison, cells were incubated with the CFTR correctors VX-809 (lumacaftor) or VX-661.

To evaluate the effect of test compounds on CFTR protein function, the activity of the CFTR chloride channel was determined by studying the efflux of iodide ions using an iodide sensitive electrode. Cells were incubated with NaI loading buffer (136 mM NaI, 3 mM $KNO_3$, 2 mM $Ca(NO_3)$, 11 mM glucose, 20 mM HEPES, pH 7.4) for 1 hour at room temperature. Extracellular NaI solution was then removed and replaced with efflux buffer in which NaI was replaced with $NaNO_3$. Samples were taken and replaced at 1 minute intervals. The first 3 samples taken before addition of the CFTR activation cocktail (time 0-2 min) were used to establish a stable baseline of ion efflux. CFTR activation cocktail (150 μM cpt-cAMP+1 mM IBMX+10 μM forskolin) was included in the efflux buffer from time 3 minutes. NaI concentration was then measured using an iodide sensitive electrode moved over each sample by a computerised autosampler and the NaI efflux rate constant k ($min^{-1}$) was calculated. Iodide efflux peaks (maximum efflux rate during stimulation—basal level) were compared.

Figure 2:
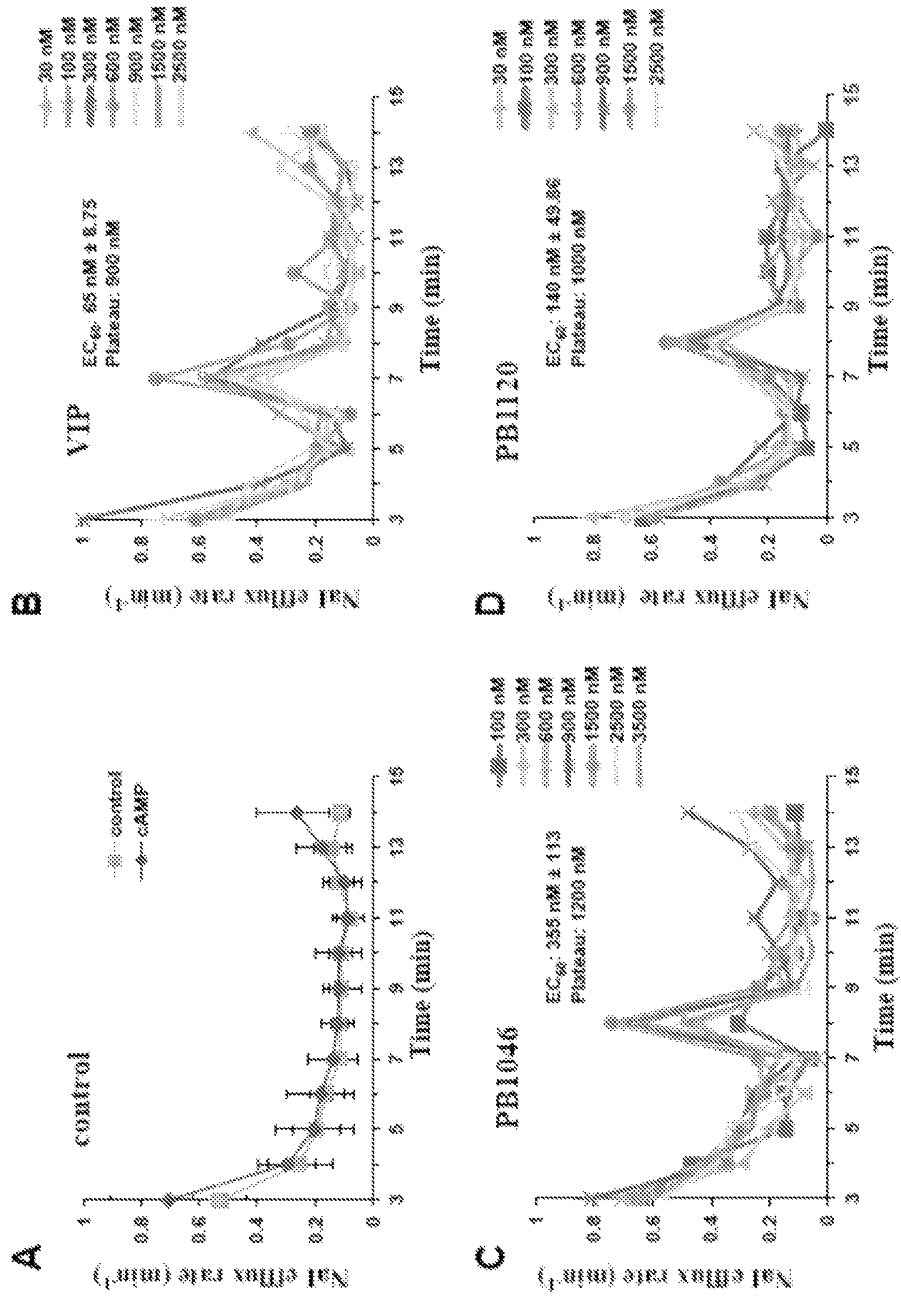
FIG. 2A-D shows the iodide efflux rates of VIP (Panel B), PB1046 (Panel C), and PB1120 (Panel D). Cells were treated with the indicated concentrations for 2 hours before stimulation with a cAMP activator cocktail. Rescued F508-delCFTR were stimulated by a cAMP activator cocktail added to the efflux buffer from time 3 to 15 minutes. Panel A shows the iodide efflux rates from JME/CF15 cells maintained at 37° C. in the absence of correctors. EC50 and plateau concentrations (n=3-5) are indicated for each compound.
Figure 3:
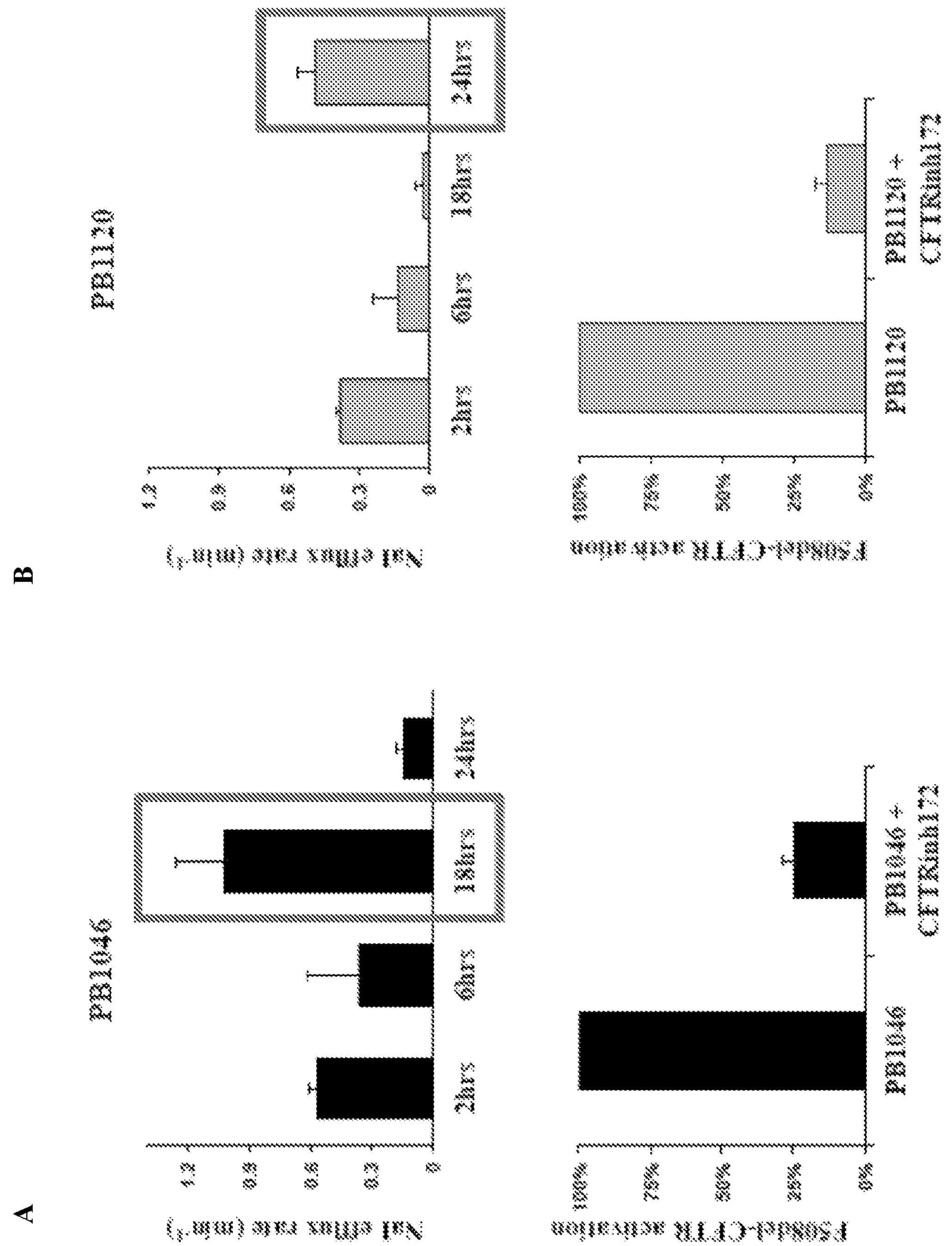
FIG. 3A-C shows the iodide efflux rates of JME/CF15 cells maintained at 37° C. and incubated with VIP, PB1046, or PB1120 as indicated for 2 to 24 hours before stimulation with a cAMP activator cocktail. Rescued F508-delCFTR were stimulated by a cAMP activator cocktail added to the efflux buffer from time 3 to 15 minutes. The lower panels show the effect of addition of the CFTR inhibitor $CFTR_{inh172}$ (20 μM) 30 minutes before and during the entire efflux experiments.
Figure 3C:
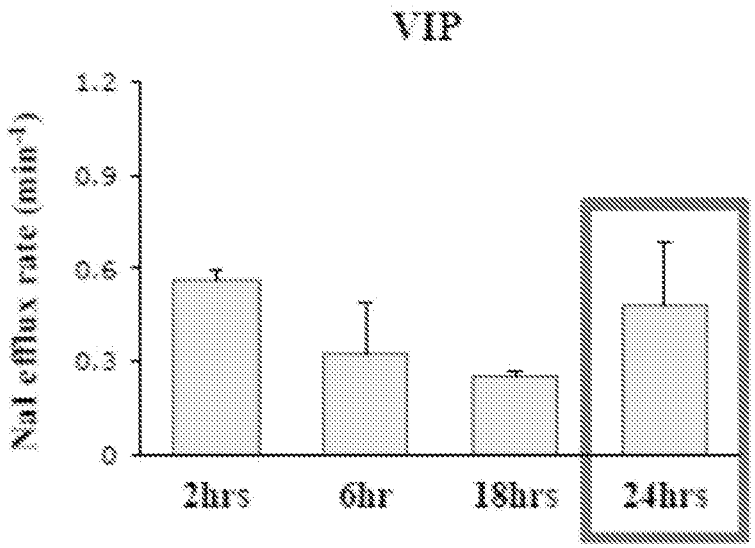
Figure 3C:
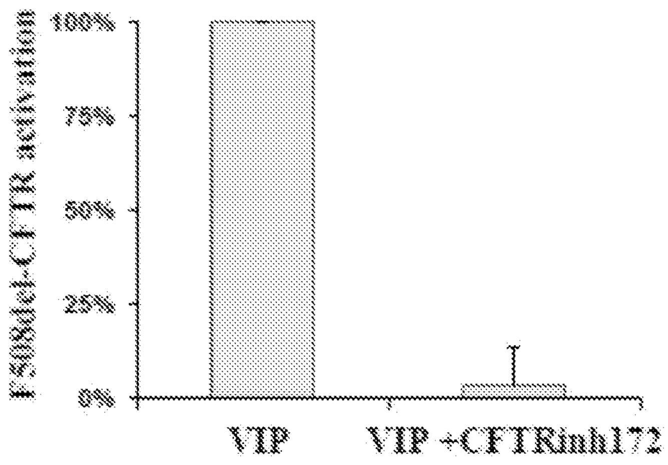

Iodide efflux rates were measured on JME/CF15 cells maintained at 37° C. and pre-incubated with VIP, PB1046, or PB1120 at 30-3,500 nM for 2 hours. FIG. 2 shows the iodide efflux rates for these agents, and Table I shows the EC50 and plateau concentrations (n=3-5) for each. Rescued F508del-CFTR was stimulated by a cAMP activator cocktail added to the efflux buffer. FIG. 3 shows the time-course of the corrector effects of these VIP therapeutics. The activity was significantly reduced when the CFTR inhibitor compound. $CFTR_{inh172}$ (20 μM) was included in the incubation, confirming that the iodide efflux was mediated by CFTR.

TABLE 1

| | VIP | PB1120 (n = 3-5) | PB1046 (n = 3-5) |
|---|---|---|---|
| $EC_{50}$ | 65 nM | 140 nM | 355 nM |
| plateau concentration | 900 nM | 1000 nM | 1200 nM |

Figure 4:
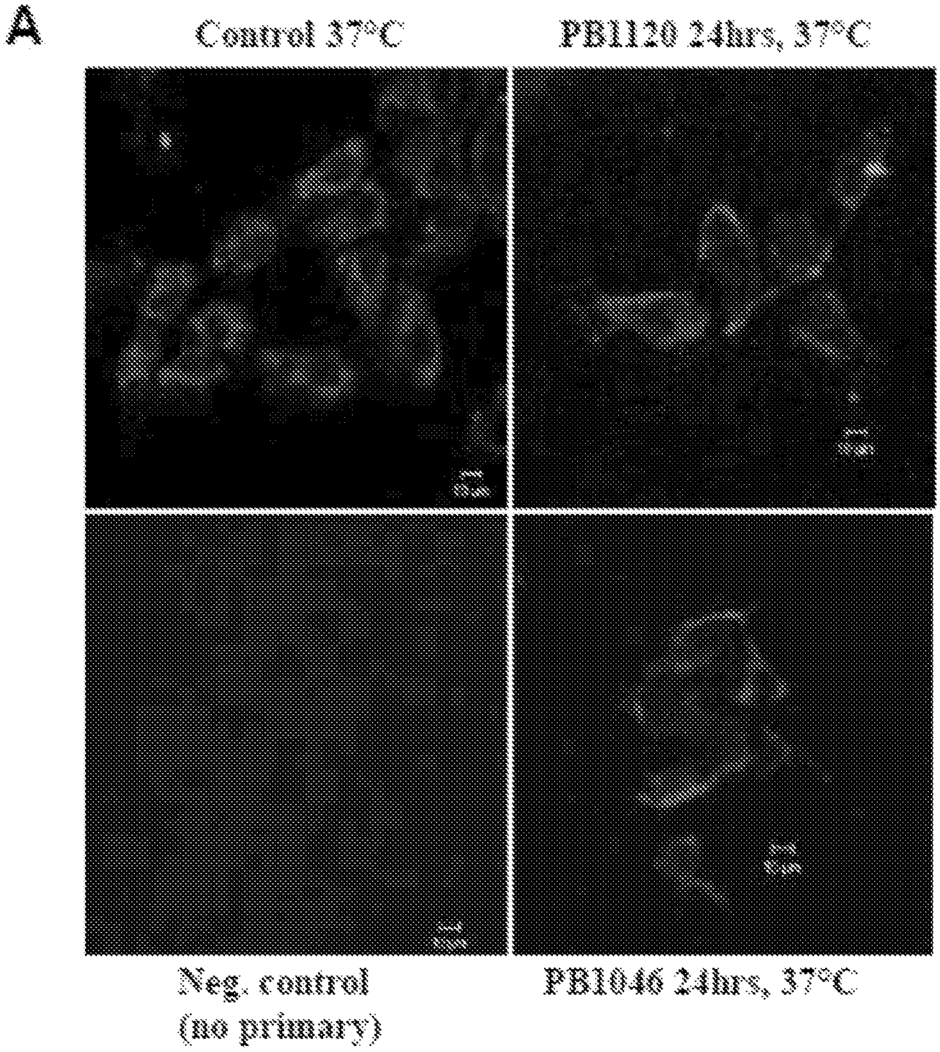
FIG. 4A-B shows the correction of F508del-CFTR maturation and membrane expression. JME/CF15 cells were immunostained for CFTR (A). Panel B shows an immunoblott of lysates from cells maintained at 37° C. and incubated with each compound for 24 hours.
Figure 4:
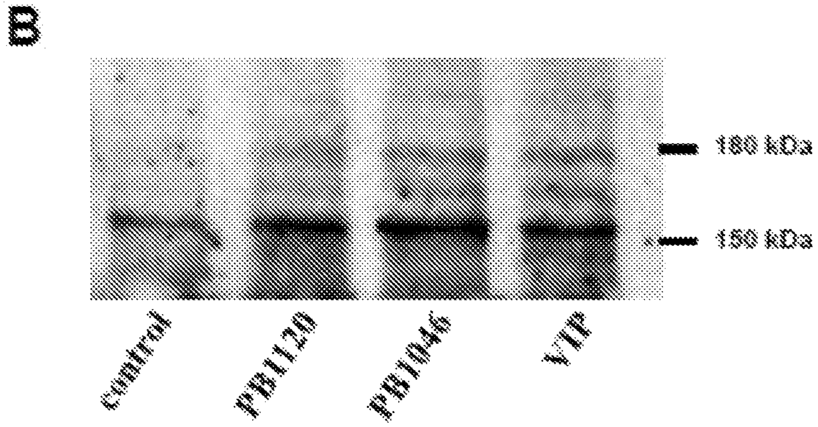

Immunoblotting was performed to visualize the localization of the F508del-CFTR in the epithelial cells treated with VIP, PB1120, or PB1046. As shown in FIG. 4, treatment with PB1120 and PB1046 corrected F508del-CFTR maturation and membrane expression.

Figure 5:
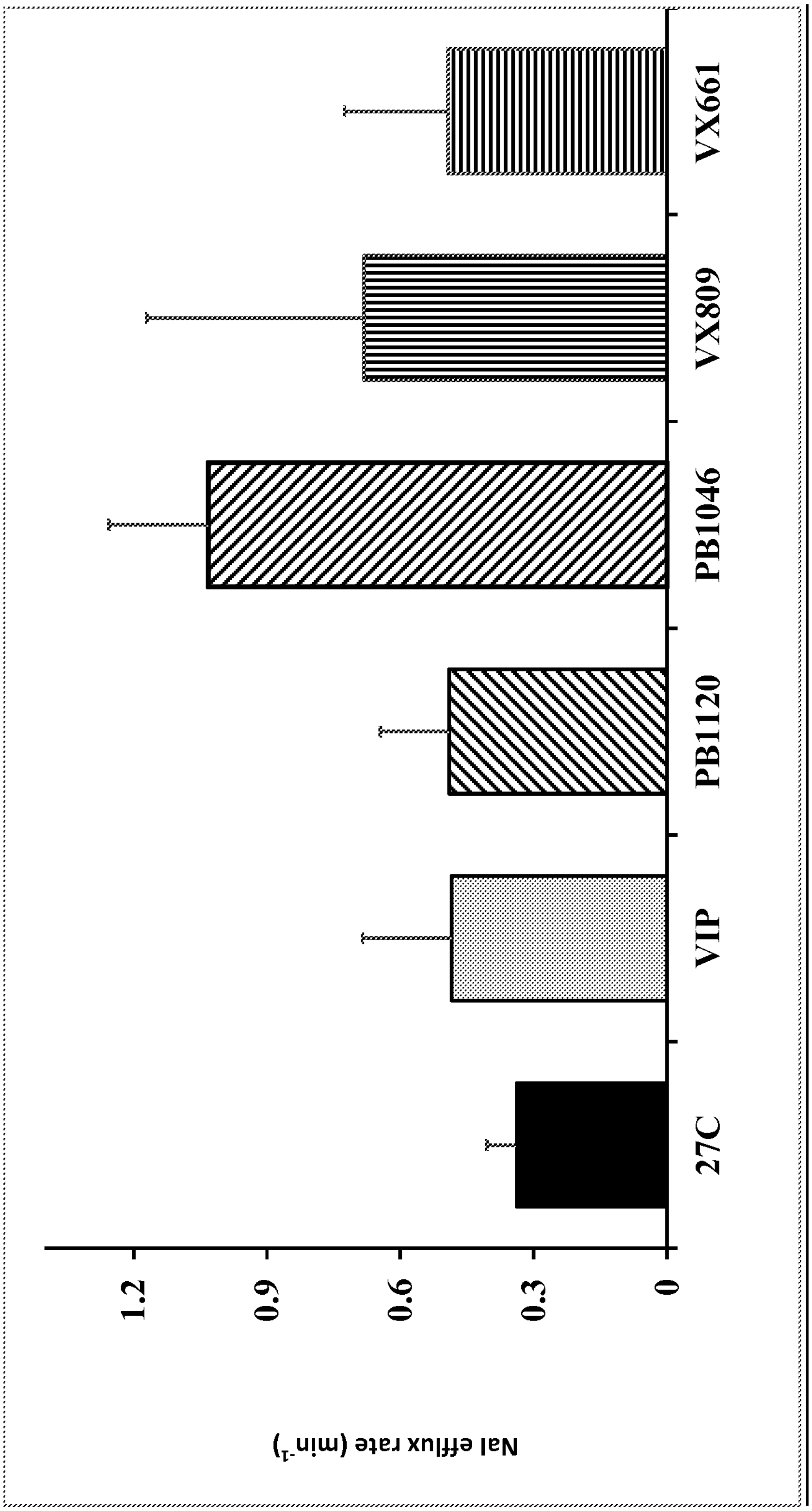
FIG. 5 shows iodide efflux rates measured on JME/CF15 cells treated with the following conditions before stimulation with a cAMP activator cocktail: (27 C) 24 hours at 27° C.; (VIP) 37° C.+treatment with 900 nM VIP for 24 hours; (PB1120) 37° C.+treatment with 1 μM PB1120 for 24 hours; (PB1046) 37° C.+treatment with 1.2 μM PB1046 for 18 hours; (VX809) 37° C.+treatment with 1 μM VX809 for 24 hours; (VX661) 37° C.+treatment with 3 μM VX661 for 24 hours. Rescued F508del-CFTR was stimulated by a cAMP activator cocktail.

Incubation of JME/CF15 cells at 27° C., rather than 37° C. allows processing of F508del-CFTR and its expression at, the cell membrane. When cells are incubated at 37° C. essentially no iodide efflux is detected above background. FIG. 5 shows that VIP, PB1046 and PB1120 were all able to correct and/or potentiate the activity of F508del-CFTR to an equivalent or greater extent than VX-809 and VX-661.

Example 2: Co-Administration of PB1120 or PB1046 with VX-770 or VX-809 has a Synergistic Effect on Rescuing F508del-CFTR Function To study the effects of administration of PB1120 or PB1046 together with CFTR potentiators or CFTR correctors, iodide efflux assays were performed as described in Example 1.

Figure 6A:
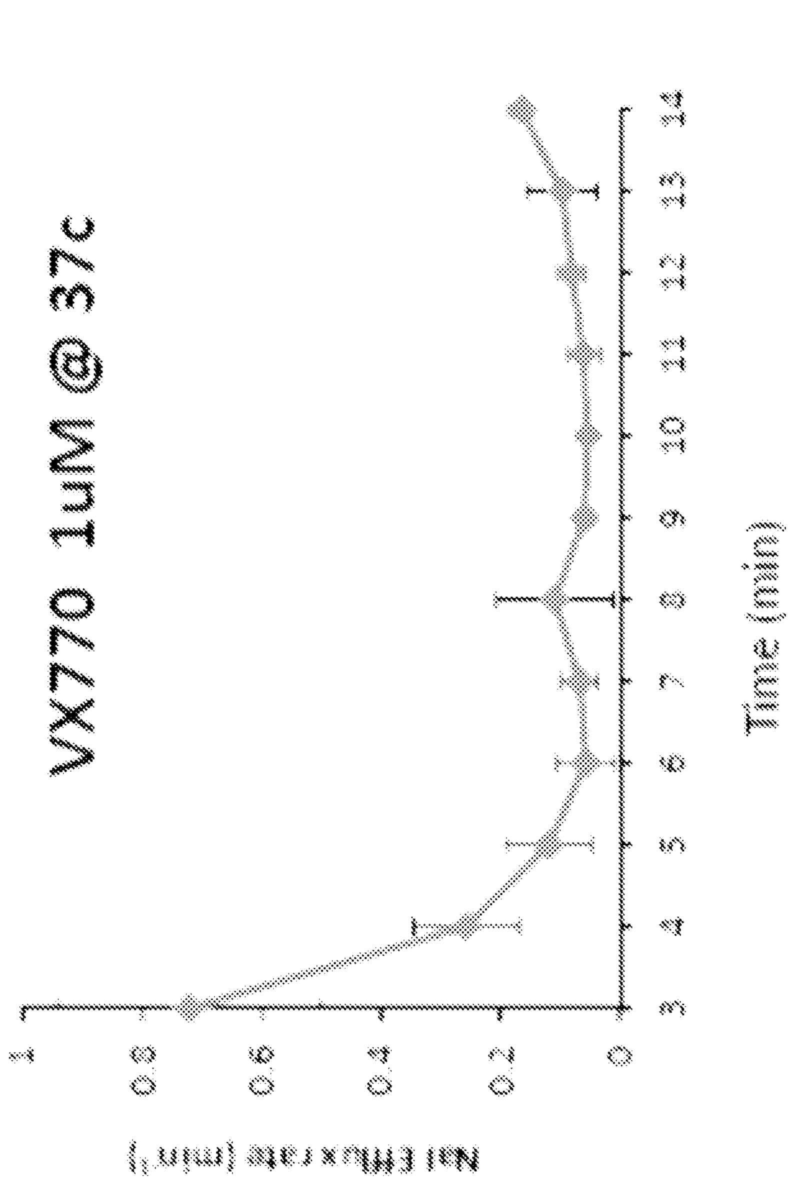
FIG. 6A-C demonstrates iodide efflux rates measured on JME/CF15 cells maintained at 37° C. Panel A shows acute treatment with 1 μM VX770 at 37° C. did not produce any significant stimulation compared to basal levels (p 0.7). Panel B shows treatment with 350 nM PB1046 for 18 hours alone or in combination with acute treatment with 1 μM VX770. Panel C shows treatment with 140 nM PB1120 for 24 hours, alone or in combination with acute treatment with 1 μM VX770. Rescued F508del-CFTR was stimulated by a cAMP activator cocktail. Administration of agents together resulted in a synergistic effect on iodide efflux.
Figure 6B:
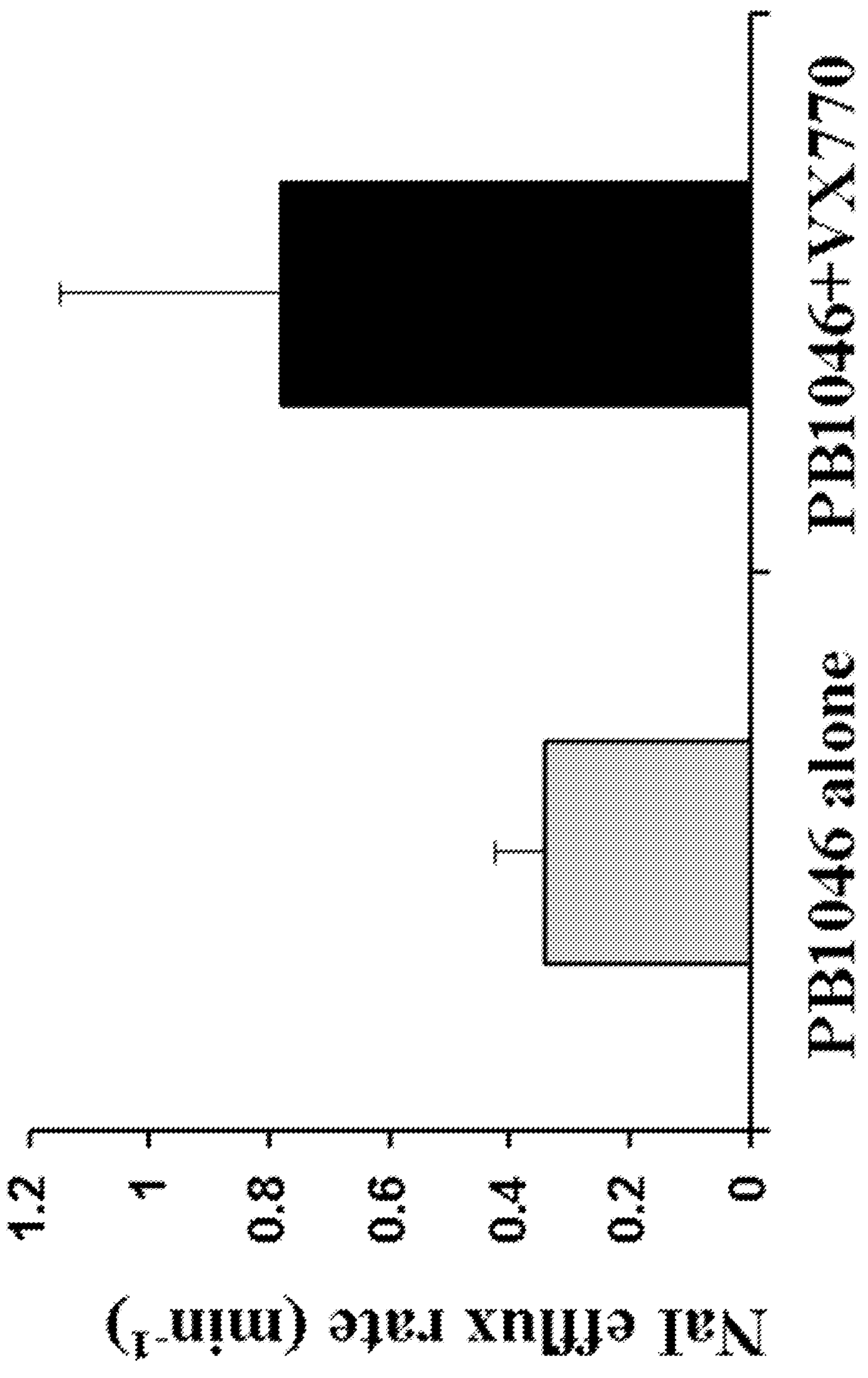
Figure 6C:
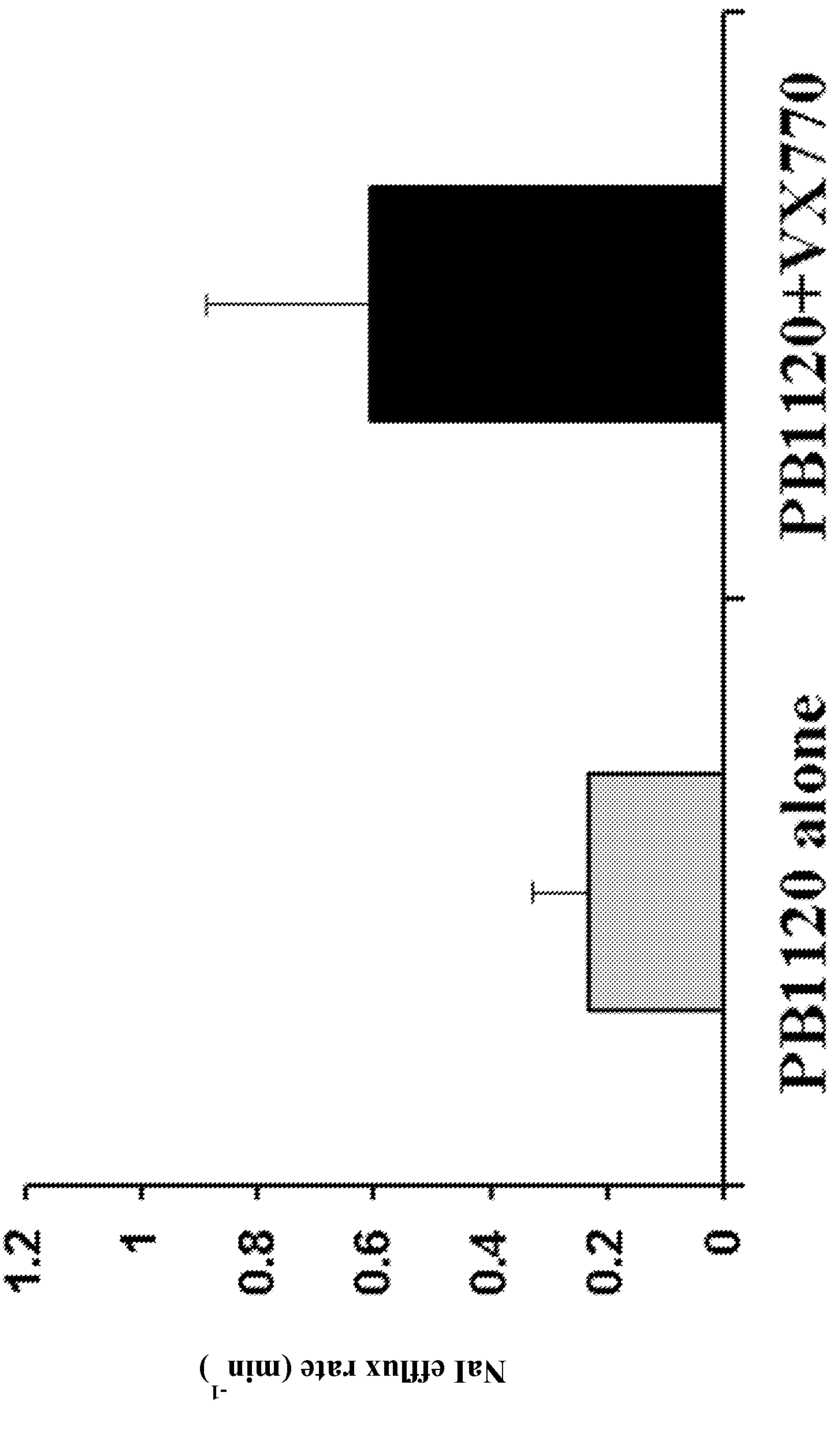
Figure 7:
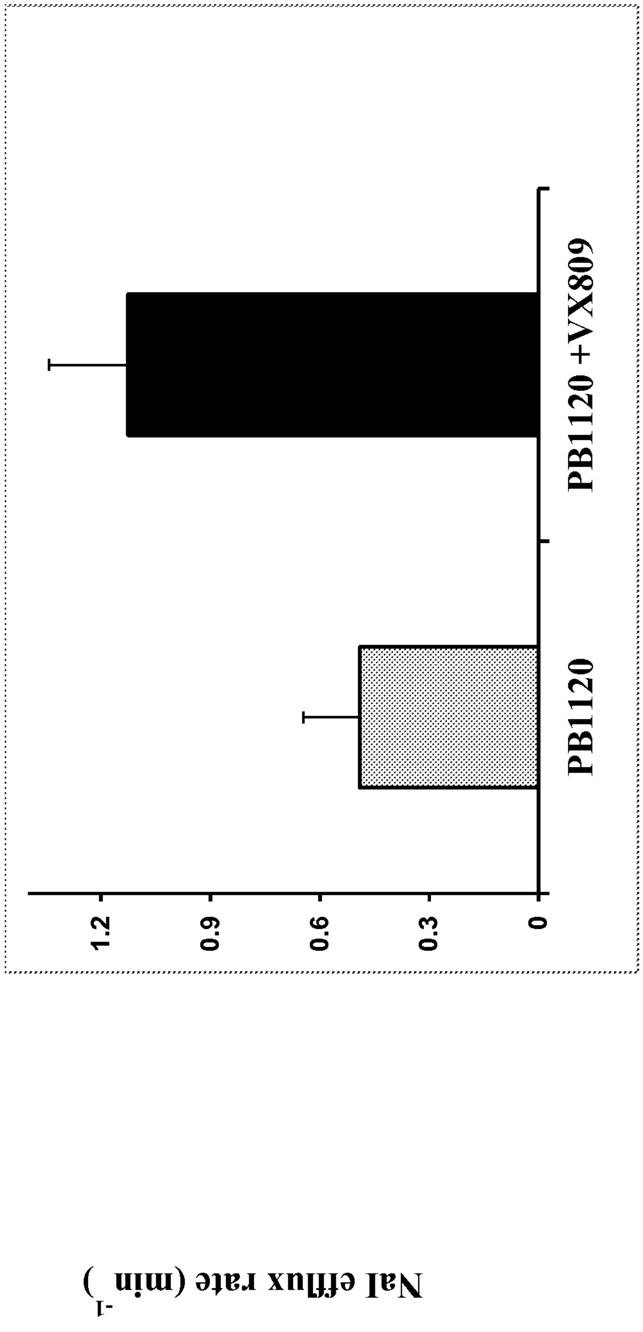
FIG. 7 demonstrates iodide efflux rates measured on JME/CF15 cells maintained at 37° C. Cells were treated with 1 PB1120 for 24 hours alone or in combination with 1 μM VX809 for 24 hours. Administration of the agents together resulted in a synergistic effect on iodide efflux.

JME/CF15 ells were acutely treated with 1 μM of the CFTR potentiator VX-770 (ivacaftor) and then treated with 350 nM PB1046 for 18 hours or 140 nM PB1120 for 24 hours. As shown in FIG. 6A, treatment with VX-770 alone demonstrated no effect on iodide efflux. However, when PB1046 or PB1120 were administered in combination with VX-770 synergistic effect on iodide efflux was observed (FIGS. 6B and C). This synergism is also seen when cells are treated with both 1 μM PB1120 and 1 μM VX-809 for 24 hours (FIG. 7).

All publications, patents, and patent publications cited are incorporated by reference herein in their entirety for all purposes.

This application incorporates by reference the following publications in their entireties for all purposes: US 2001/0034050; US 2009/0220455; U.S. Pat. No. 8,334,257; US 2013/0310538; US 2013/0172274; US 2011/0236384; U.S. Pat. Nos. 6,582,926; 7,429,458; 7,364,859; 8,178,495; US 2013/0079277; US 2013/0085099; US 2013/0143802; US 2014/0024600; US 2011/0178017; U.S. Pat. No. 7,709,227; US 2011/0123487; U.S. Pat. No. 8,729,018; US 2014/0171370; US 2013/0150291; WO/2014/113434; US 2014/0213516; U.S. Application No. 62/082,945 filed Nov. 21, 2014; US Application No. 62/113,943 filed. Feb. 9, 2015; and US Application No. 62/145,770 filed Apr. 10, 2015.

REFERENCES

Aliakbari et al. (1978) Selective localization of vasoactive intestinal peptide and substance P in human eosinophils. *Biochem. Biophys. Res. Comm.* 148(3): 1440-1445.

Alshafie et al. (2014). *Am. J. Physiol-Cell Physiol.* 307(1): C107-109.

Chappe et al. (2008) VIP increases CFTR levels in the apical membrane of calu-3 cells through a PKC-dependent mechanism. *J. Pharmacol Exp. Ther.* 327:226-38.

Chappe and Said (2012) VIP as a Corrector of CFTR Trafficking and membrane stability. In *Cystic Fibrosis—Renewed Elopes Through Research*. D. Sriramulu (Ed.).

Choi et al, (2007) Synergistic airway gland mucus secretion in response to vasoactive intestinal peptide and carbachol is lost in cystic fibrosis. *J. Clin. Invest* 117(10):3118-3127.

Cutz et al. (1978) Release of vasoactive intestinal polypeptide in last cells by histamine liberators. *Nature.* 275:661-662.

Derand et al. (2004) Activation of VPAC1 receptors by VIP and PACAP-27 in human bronchial epithelial cells induces CFTR-dependent chloride secretion. *Br. J. Pharmacol.* 141:698-708.

Heinz-Erian et al. (1985) Deficient vasoactive intestinal peptide innervation in the sweat glands of cystic fibrosis patients. *Science* 229:1407-8.

Heinz-Erian et al. (1986) Receptors for vasoactive intestinal peptide on isolated human sweat glands. *Peptides.* 7Suppl. 1:151-154.

Jefferson et al. (1990) Expression of normal and cystic fibrosis phenotypes by continuous airway epithelial cell lines. *Am J Physiol Lung Cell Mol Physiol* 259: L496-L505.

Joo et al. (2002) Absent secretion to vasoactive intestinal peptide in cystic fibrosis airway glands. *JBC.* 277(52): 50710-5.

Joo et al. (2010) Hyposecretion of fluid from tracheal submucosal glands of CFTR-deficient pigs. *The J. Clin. Invest.* 120(9):3161-3166.

Li and Naren (2010) CFTR Chloride Channel in the Apical Compartments: Spatiotemporal Coupling to its Interacting Partners. *Integr Biol* (*Camb*) April 7; 2(4): 161-177.

Lundberg et al. (1980) Vasoactive intestinal polypeptide cholinergic neurons of exocrine glands: Functional significance of coexisting transmitters for vasodilation and secretion. *PNAS.* 77(3):1651-5.

Raju et al. (2013) Cigarette smoke induces systemic defects in Cystic Fibrosis Transmembrane Conductance Regulator Function. *Am. J. Respir. Crit. Care. Med.* 188:1321-1330.

Riordan et al. (1989) Identification of the cystic fibrosis gene: cloning and characterization of complementary DNA. *Science.* 245:1066-1073.

Rowe and Verkman (2013) Cystic Fibrosis Transmembrane Regulator Correctors and Potentiators. *Cold Spring Harb Perspect Med;* 3a009761.

Sloane et al. (2012) A pharmacologic approach to acquired Cystic Fibrosis transmembrane conductance regulator dysfunction in smoking related lung disease. *PLOS One.* 7:e39809.

Quinton P M, (1983) Chloride impermeability in cystic fibrosis. *Nature* 301:421-422.

*Therapeutic Proteins: Strategies to Modulate Their Plasma Half-Life*. Kontermann, R. (Ed.) Wiley-Blackwell Press. (2012) pp. 7-9

Wine et al. (2007) Parasympathetic control of airway submucosal glands: Central reflexes and the airway intrinsic nervous system. *Autonomic Neuroscience: Basic & Clinical.* 133:35-54.

Wu et al. (2011) Prospect of vasoactive intestinal peptide therapy for COPD/PAH and asthma: A review. *Respiratory Res.* 12:45-9921-12-45.

The invention claimed is:

1. A method for treating cystic fibrosis comprising subcutaneously administering to a patient in need thereof a pharmaceutical composition comprising a fusion protein comprising a VPAC2-selective Vasoactive Intestinal Peptide (VIP) and one or more elastin-like peptides (ELP).

2. The method of claim 1, wherein the ELP comprises repeat units of any of SEQ ID NOs: 1-13, or a combination thereof.

3. The method of claim 2, wherein the ELP comprises repeat units of VPGXG (SEQ ID NO:3).

4. The method of claim 3, wherein the ELP comprises 120 repeat units of VPGXG (SEQ ID NO:3), where X is independently selected from Val, Ala, and Gly.

5. The method of claim 4, wherein X is independently selected from Val, Ala, and Gly in a ratio of about 5:2:3.

6. The method of claim 1, wherein the pharmaceutical composition is formulated for systemic delivery.

7. The method of claim 1, wherein the pharmaceutical composition comprises SEQ ID NO: 15.

8. The method of claim 1, wherein the pharmaceutical composition is formulated for sustained release.

9. The method of claim 1, wherein the pharmaceutical composition is administered with one or more additional cystic fibrosis therapies or therapies to treat disorders associated with CFTR protein dysfunction.

10. The method of claim 9, wherein the one or more additional cystic fibrosis therapies is selected from the group consisting of Cystic Fibrosis Transmembrane Conductance Regulator (CFTR) potentiators, CFTR correctors, nonsense mutation readthrough agents, CFTR production correctors, read-through agents, small molecule ion channel agents, osmotic agents, gene therapy, RNA repair, soluble guanylate cyclase stimulators, S-nitrosoglutathione reductase inhibitors, DNase, antibiotics, antifungals, mucolytics, bronchodilators, nitric oxide, anticholinergics, nonsteroidal anti-inflammatory drugs (NSAIDs), membrane stabilizers, corticosteroids, and enzyme replacement therapy.

11. The method of claim 10, wherein the CFTR potentiator is selected from the group consisting of ivacaftor (VX-770) and QBW251.

12. The method of claim 10, wherein the CFTR corrector is selected from the group consisting of lumacaftor (VX-809) and VX-661.

13. The method of claim 1, wherein the patient has at least one or more mutations in a CFTR gene.

14. The method of claim 13, wherein the patient is homozygous for the one or more mutations in the CFTR gene.

15. The method of claim 13, wherein the patient is heterozygous for the one or more mutations in the CFTR gene.

16. The method of claim 13, wherein the patient has an F508del mutation.

* * * * *

SEQUENCE LISTING

```
<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: ELP component sequence

<400> SEQUENCE: 1

Val Pro Gly Gly
1


<210> SEQ ID NO 2
<211> LENGTH: 4
<212> TYPE: PRT
<213> ORGANISM: Artificial Sequence
<220> FEATURE:
<223> OTHER INFORMATION: ELP component sequence

<400> SEQUENCE: 2

Ile Pro Gly Gly
1


<210> SEQ ID NO 3
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or
      non-natural amino acid

<400> SEQUENCE: 3

Val Pro Gly Xaa Gly
1               5


<210> SEQ ID NO 4
<211> LENGTH: 5
<212> TYPE: PRT
<213> ORGANISM: Artificial Sequence
<220> FEATURE:
<223> OTHER INFORMATION: ELP component sequence

<400> SEQUENCE: 4

Ala Val Gly Val Pro
1               5


<210> SEQ ID NO 5
<211> LENGTH: 5
<212> TYPE: PRT
<213> ORGANISM: Artificial Sequence
<220> FEATURE:
<223> OTHER INFORMATION: ELP component sequence
<220> FEATURE:
```

<221> NAME/KEY: misc_feature
<222> LOCATION: (4)..(4)
<223> OTHER INFORMATION: Xaa can be any naturally occurring or
      non-natural amino acid

<400> SEQUENCE: 5

Ile Pro Gly Xaa Gly
1               5

<210> SEQ ID NO 6
<211> LENGTH: 5
<212> TYPE: PRT
<213> ORGANISM: Artificial Sequence
<220> FEATURE:
<223> OTHER INFORMATION: ELP component sequence

<400> SEQUENCE: 6

Ile Pro Gly Val Gly
1               5

<210> SEQ ID NO 7
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or
      non-natural amino acid

<400> SEQUENCE: 7

Leu Pro Gly Xaa Gly
1               5

<210> SEQ ID NO 8
<211> LENGTH: 5
<212> TYPE: PRT
<213> ORGANISM: Artificial Sequence
<220> FEATURE:
<223> OTHER INFORMATION: ELP component sequence

<400> SEQUENCE: 8

Leu Pro Gly Val Gly
1               5

<210> SEQ ID NO 9
<211> LENGTH: 6
<212> TYPE: PRT
<213> ORGANISM: Artificial Sequence
<220> FEATURE:
<223> OTHER INFORMATION: ELP component sequence

<400> SEQUENCE: 9

Val Ala Pro Gly Val Gly
1               5

<210> SEQ ID NO 10
<211> LENGTH: 8
<212> TYPE: PRT
<213> ORGANISM: Artificial Sequence
<220> FEATURE:
<223> OTHER INFORMATION: ELP component sequence

<400> SEQUENCE: 10

Gly Val Gly Val Pro Gly Val Gly
1               5

-continued

<210> SEQ ID NO 11
<211> LENGTH: 9
<212> TYPE: PRT
<213> ORGANISM: Artificial Sequence
<220> FEATURE:
<223> OTHER INFORMATION: ELP component sequence

<400> SEQUENCE: 11

Val Pro Gly Phe Gly Val Gly Ala Gly
1               5

<210> SEQ ID NO 12
<211> LENGTH: 9
<212> TYPE: PRT
<213> ORGANISM: Artificial Sequence
<220> FEATURE:
<223> OTHER INFORMATION: ELP component sequence

<400> SEQUENCE: 12

Val Pro Gly Val Gly Val Pro Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (1)..(1)
<223> OTHER INFORMATION: Xaa can be any naturally occurring or
      non-natural amino acid

<400> SEQUENCE: 13

Xaa Pro Gly Val Gly
1               5

<210> SEQ ID NO 14
<211> LENGTH: 29
<212> TYPE: PRT
<213> ORGANISM: Artificial Sequence
<220> FEATURE:
<223> OTHER INFORMATION: M-VIP

<400> SEQUENCE: 14

Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn
            20                  25

<210> SEQ ID NO 15
<211> LENGTH: 634
<212> TYPE: PRT
<213> ORGANISM: Artificial Sequence
<220> FEATURE:
<223> OTHER INFORMATION: M-VIP ELP1-120

<400> SEQUENCE: 15

Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn Val Pro Gly
            20                  25                  30

Val Gly Val Pro Gly Val Gly Val Pro Gly Gly Gly Val Pro Gly Ala
        35                  40                  45

-continued

```
Gly Val Pro Gly Val Gly Val Pro Gly Val Gly Val Pro Gly Val Gly
    50                  55                  60

Val Pro Gly Gly Gly Val Pro Gly Ala Gly Val Pro Gly Gly Gly Val
65                  70                  75                  80

Pro Gly Val Gly Val Pro Gly Val Gly Val Pro Gly Gly Gly Val Pro
                85                  90                  95

Gly Ala Gly Val Pro Gly Val Gly Val Pro Gly Val Gly Val Pro Gly
            100                 105                 110

Val Gly Val Pro Gly Gly Gly Val Pro Gly Ala Gly Val Pro Gly Gly
        115                 120                 125

Gly Val Pro Gly Val Gly Val Pro Gly Val Gly Val Pro Gly Gly Gly
    130                 135                 140

Val Pro Gly Ala Gly Val Pro Gly Val Gly Val Pro Gly Val Gly Val
145                 150                 155                 160

Pro Gly Val Gly Val Pro Gly Gly Gly Val Pro Gly Ala Gly Val Pro
                165                 170                 175

Gly Gly Gly Val Pro Gly Val Gly Val Pro Gly Val Gly Val Pro Gly
            180                 185                 190

Gly Gly Val Pro Gly Ala Gly Val Pro Gly Val Gly Val Pro Gly Val
        195                 200                 205

Gly Val Pro Gly Val Gly Val Pro Gly Gly Gly Val Pro Gly Ala Gly
    210                 215                 220

Val Pro Gly Gly Gly Val Pro Gly Val Gly Val Pro Gly Val Gly Val
225                 230                 235                 240

Pro Gly Gly Gly Val Pro Gly Ala Gly Val Pro Gly Val Gly Val Pro
                245                 250                 255

Gly Val Gly Val Pro Gly Val Gly Val Pro Gly Gly Gly Val Pro Gly
            260                 265                 270

Ala Gly Val Pro Gly Gly Gly Val Pro Gly Val Gly Val Pro Gly Val
        275                 280                 285

Gly Val Pro Gly Gly Gly Val Pro Gly Ala Gly Val Pro Gly Val Gly
    290                 295                 300

Val Pro Gly Val Gly Val Pro Gly Val Gly Val Pro Gly Gly Gly Val
305                 310                 315                 320

Pro Gly Ala Gly Val Pro Gly Gly Gly Val Pro Gly Val Gly Val Pro
                325                 330                 335

Gly Val Gly Val Pro Gly Gly Gly Val Pro Gly Ala Gly Val Pro Gly
            340                 345                 350

Val Gly Val Pro Gly Val Gly Val Pro Gly Val Gly Val Pro Gly Gly
        355                 360                 365

Gly Val Pro Gly Ala Gly Val Pro Gly Gly Gly Val Pro Gly Val Gly
    370                 375                 380

Val Pro Gly Val Gly Val Pro Gly Gly Gly Val Pro Gly Ala Gly Val
385                 390                 395                 400

Pro Gly Val Gly Val Pro Gly Val Gly Val Pro Gly Val Gly Val Pro
                405                 410                 415

Gly Gly Gly Val Pro Gly Ala Gly Val Pro Gly Gly Gly Val Pro Gly
            420                 425                 430

Val Gly Val Pro Gly Val Gly Val Pro Gly Gly Gly Val Pro Gly Ala
        435                 440                 445

Gly Val Pro Gly Val Gly Val Pro Gly Val Gly Val Pro Gly Val Gly
    450                 455                 460
```

-continued

```
Val Pro Gly Gly Gly Val Pro Gly Ala Gly Val Pro Gly Gly Gly Val
465                 470                 475                 480

Pro Gly Val Gly Val Pro Gly Val Gly Val Pro Gly Gly Gly Val Pro
                485                 490                 495

Gly Ala Gly Val Pro Gly Val Gly Val Pro Gly Val Gly Val Pro Gly
            500                 505                 510

Val Gly Val Pro Gly Gly Gly Val Pro Gly Ala Gly Val Pro Gly Gly
        515                 520                 525

Gly Val Pro Gly Val Gly Val Pro Gly Val Gly Val Pro Gly Gly Gly
    530                 535                 540

Val Pro Gly Ala Gly Val Pro Gly Val Gly Val Pro Gly Val Gly Val
545                 550                 555                 560

Pro Gly Val Gly Val Pro Gly Gly Gly Val Pro Gly Ala Gly Val Pro
                565                 570                 575

Gly Gly Gly Val Pro Gly Val Gly Val Pro Gly Val Gly Val Pro Gly
            580                 585                 590

Gly Gly Val Pro Gly Ala Gly Val Pro Gly Val Gly Val Pro Gly Val
        595                 600                 605

Gly Val Pro Gly Val Gly Val Pro Gly Gly Gly Val Pro Gly Ala Gly
    610                 615                 620

Val Pro Gly Gly Gly Val Pro Gly Trp Pro
625                 630


<210> SEQ ID NO 16
<211> LENGTH: 636
<212> TYPE: PRT
<213> ORGANISM: Artificial Sequence
<220> FEATURE:
<223> OTHER INFORMATION: MAA-VIP ELP1-120

<400> SEQUENCE: 16

Met Ala Ala His Ser Asp Ala Val Phe Thr Asp Asn Tyr Thr Arg Leu
1               5                   10                  15

Arg Lys Gln Met Ala Val Lys Lys Tyr Leu Asn Ser Ile Leu Asn Val
            20                  25                  30

Pro Gly Val Gly Val Pro Gly Val Gly Val Pro Gly Gly Gly Val Pro
        35                  40                  45

Gly Ala Gly Val Pro Gly Val Gly Val Pro Gly Val Gly Val Pro Gly
    50                  55                  60

Val Gly Val Pro Gly Gly Gly Val Pro Gly Ala Gly Val Pro Gly Gly
65                  70                  75                  80

Gly Val Pro Gly Val Gly Val Pro Gly Val Gly Val Pro Gly Gly Gly
                85                  90                  95

Val Pro Gly Ala Gly Val Pro Gly Val Gly Val Pro Gly Val Gly Val
            100                 105                 110

Pro Gly Val Gly Val Pro Gly Gly Gly Val Pro Gly Ala Gly Val Pro
        115                 120                 125

Gly Gly Gly Val Pro Gly Val Gly Val Pro Gly Val Gly Val Pro Gly
    130                 135                 140

Gly Gly Val Pro Gly Ala Gly Val Pro Gly Val Gly Val Pro Gly Val
145                 150                 155                 160

Gly Val Pro Gly Val Gly Val Pro Gly Gly Gly Val Pro Gly Ala Gly
                165                 170                 175

Val Pro Gly Gly Gly Val Pro Gly Val Gly Val Pro Gly Val Gly Val
            180                 185                 190
```

-continued

```
Pro Gly Gly Gly Val Pro Gly Ala Gly Val Pro Gly Val Gly Val Pro
        195                 200                 205

Gly Val Gly Val Pro Gly Val Gly Val Pro Gly Gly Gly Val Pro Gly
    210                 215                 220

Ala Gly Val Pro Gly Gly Gly Val Pro Gly Val Gly Val Pro Gly Val
225                 230                 235                 240

Gly Val Pro Gly Gly Gly Val Pro Gly Ala Gly Val Pro Gly Val Gly
                245                 250                 255

Val Pro Gly Val Gly Val Pro Gly Val Gly Val Pro Gly Gly Gly Val
            260                 265                 270

Pro Gly Ala Gly Val Pro Gly Gly Gly Val Pro Gly Val Gly Val Pro
        275                 280                 285

Gly Val Gly Val Pro Gly Gly Gly Val Pro Gly Ala Gly Val Pro Gly
    290                 295                 300

Val Gly Val Pro Gly Val Gly Val Pro Gly Val Gly Val Pro Gly Gly
305                 310                 315                 320

Gly Val Pro Gly Ala Gly Val Pro Gly Gly Gly Val Pro Gly Val Gly
                325                 330                 335

Val Pro Gly Val Gly Val Pro Gly Gly Gly Val Pro Gly Ala Gly Val
            340                 345                 350

Pro Gly Val Gly Val Pro Gly Val Gly Val Pro Gly Val Gly Val Pro
        355                 360                 365

Gly Gly Gly Val Pro Gly Ala Gly Val Pro Gly Gly Gly Val Pro Gly
    370                 375                 380

Val Gly Val Pro Gly Val Gly Val Pro Gly Gly Gly Val Pro Gly Ala
385                 390                 395                 400

Gly Val Pro Gly Val Gly Val Pro Gly Val Gly Val Pro Gly Val Gly
                405                 410                 415

Val Pro Gly Gly Gly Val Pro Gly Ala Gly Val Pro Gly Gly Gly Val
            420                 425                 430

Pro Gly Val Gly Val Pro Gly Val Gly Val Pro Gly Gly Gly Val Pro
        435                 440                 445

Gly Ala Gly Val Pro Gly Val Gly Val Pro Gly Val Gly Val Pro Gly
    450                 455                 460

Val Gly Val Pro Gly Gly Gly Val Pro Gly Ala Gly Val Pro Gly Gly
465                 470                 475                 480

Gly Val Pro Gly Val Gly Val Pro Gly Val Gly Val Pro Gly Gly Gly
                485                 490                 495

Val Pro Gly Ala Gly Val Pro Gly Val Gly Val Pro Gly Val Gly Val
            500                 505                 510

Pro Gly Val Gly Val Pro Gly Gly Gly Val Pro Gly Ala Gly Val Pro
        515                 520                 525

Gly Gly Gly Val Pro Gly Val Gly Val Pro Gly Val Gly Val Pro Gly
    530                 535                 540

Gly Gly Val Pro Gly Ala Gly Val Pro Gly Val Gly Val Pro Gly Val
545                 550                 555                 560

Gly Val Pro Gly Val Gly Val Pro Gly Gly Gly Val Pro Gly Ala Gly
                565                 570                 575

Val Pro Gly Gly Gly Val Pro Gly Val Gly Val Pro Gly Val Gly Val
            580                 585                 590

Pro Gly Gly Gly Val Pro Gly Ala Gly Val Pro Gly Val Gly Val Pro
        595                 600                 605

Gly Val Gly Val Pro Gly Val Gly Val Pro Gly Gly Gly Val Pro Gly
```

```
    610                 615                 620

Ala Gly Val Pro Gly Gly Gly Val Pro Gly Trp Pro
625                 630                 635


<210> SEQ ID NO 17
<211> LENGTH: 28
<212> TYPE: PRT
<213> ORGANISM: Homo sapiens

<400> SEQUENCE: 17

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25


<210> SEQ ID NO 18
<211> LENGTH: 50
<212> TYPE: PRT
<213> ORGANISM: Artificial Sequence
<220> FEATURE:
<223> OTHER INFORMATION: M-VIP-ELP1

<400> SEQUENCE: 18

Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn Val Pro Gly
            20                  25                  30

Val Gly Val Pro Gly Val Gly Val Pro Gly Gly Gly Val Pro Gly Ala
        35                  40                  45

Gly Val
    50


<210> SEQ ID NO 19
<211> LENGTH: 50
<212> TYPE: PRT
<213> ORGANISM: Artificial Sequence
<220> FEATURE:
<223> OTHER INFORMATION: MAA-VIP

<400> SEQUENCE: 19

Met Ala Ala His Ser Asp Ala Val Phe Thr Asp Asn Tyr Thr Arg Leu
1               5                   10                  15

Arg Lys Gln Met Ala Val Lys Lys Tyr Leu Asn Ser Ile Leu Asn Val
            20                  25                  30

Pro Gly Val Gly Val Pro Gly Val Gly Val Pro Gly Gly Gly Val Pro
        35                  40                  45

Gly Ala
    50


<210> SEQ ID NO 20
<211> LENGTH: 633
<212> TYPE: PRT
<213> ORGANISM: Artificial Sequence
<220> FEATURE:
<223> OTHER INFORMATION: VIP ELP1-120

<400> SEQUENCE: 20

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn Val Pro Gly Val
            20                  25                  30
```

-continued

```
Gly Val Pro Gly Val Gly Val Pro Gly Gly Gly Val Pro Gly Ala Gly
        35                  40                  45

Val Pro Gly Val Gly Val Pro Gly Val Gly Val Pro Gly Val Gly Val
    50                  55                  60

Pro Gly Gly Gly Val Pro Gly Ala Gly Val Pro Gly Gly Gly Val Pro
65                  70                  75                  80

Gly Val Gly Val Pro Gly Val Gly Val Pro Gly Gly Gly Val Pro Gly
                85                  90                  95

Ala Gly Val Pro Gly Val Gly Val Pro Gly Val Gly Val Pro Gly Val
            100                 105                 110

Gly Val Pro Gly Gly Gly Val Pro Gly Ala Gly Val Pro Gly Gly Gly
        115                 120                 125

Val Pro Gly Val Gly Val Pro Gly Val Gly Val Pro Gly Gly Gly Val
    130                 135                 140

Pro Gly Ala Gly Val Pro Gly Val Gly Val Pro Gly Val Gly Val Pro
145                 150                 155                 160

Gly Val Gly Val Pro Gly Gly Gly Val Pro Gly Ala Gly Val Pro Gly
                165                 170                 175

Gly Gly Val Pro Gly Val Gly Val Pro Gly Val Gly Val Pro Gly Gly
            180                 185                 190

Gly Val Pro Gly Ala Gly Val Pro Gly Val Gly Val Pro Gly Val Gly
        195                 200                 205

Val Pro Gly Val Gly Val Pro Gly Gly Gly Val Pro Gly Ala Gly Val
    210                 215                 220

Pro Gly Gly Gly Val Pro Gly Val Gly Val Pro Gly Val Gly Val Pro
225                 230                 235                 240

Gly Gly Gly Val Pro Gly Ala Gly Val Pro Gly Val Gly Val Pro Gly
                245                 250                 255

Val Gly Val Pro Gly Val Gly Val Pro Gly Gly Gly Val Pro Gly Ala
            260                 265                 270

Gly Val Pro Gly Gly Gly Val Pro Gly Val Gly Val Pro Gly Val Gly
        275                 280                 285

Val Pro Gly Gly Gly Val Pro Gly Ala Gly Val Pro Gly Val Gly Val
    290                 295                 300

Pro Gly Val Gly Val Pro Gly Val Gly Val Pro Gly Gly Gly Val Pro
305                 310                 315                 320

Gly Ala Gly Val Pro Gly Gly Gly Val Pro Gly Val Gly Val Pro Gly
                325                 330                 335

Val Gly Val Pro Gly Gly Gly Val Pro Gly Ala Gly Val Pro Gly Val
            340                 345                 350

Gly Val Pro Gly Val Gly Val Pro Gly Val Gly Val Pro Gly Gly Gly
        355                 360                 365

Val Pro Gly Ala Gly Val Pro Gly Gly Gly Val Pro Gly Val Gly Val
    370                 375                 380

Pro Gly Val Gly Val Pro Gly Gly Gly Val Pro Gly Ala Gly Val Pro
385                 390                 395                 400

Gly Val Gly Val Pro Gly Val Gly Val Pro Gly Val Gly Val Pro Gly
                405                 410                 415

Gly Gly Val Pro Gly Ala Gly Val Pro Gly Gly Gly Val Pro Gly Val
            420                 425                 430

Gly Val Pro Gly Val Gly Val Pro Gly Gly Gly Val Pro Gly Ala Gly
        435                 440                 445

Val Pro Gly Val Gly Val Pro Gly Val Gly Val Pro Gly Val Gly Val
```

-continued

```
    450                 455                 460

Pro Gly Gly Gly Val Pro Gly Ala Gly Val Pro Gly Gly Gly Val Pro
465                 470                 475                 480

Gly Val Gly Val Pro Gly Val Gly Val Pro Gly Gly Gly Val Pro Gly
                485                 490                 495

Ala Gly Val Pro Gly Val Gly Val Pro Gly Val Gly Val Pro Gly Val
            500                 505                 510

Gly Val Pro Gly Gly Gly Val Pro Gly Ala Gly Val Pro Gly Gly Gly
        515                 520                 525

Val Pro Gly Val Gly Val Pro Gly Val Gly Val Pro Gly Gly Gly Val
    530                 535                 540

Pro Gly Ala Gly Val Pro Gly Val Gly Val Pro Gly Val Gly Val Pro
545                 550                 555                 560

Gly Val Gly Val Pro Gly Gly Gly Val Pro Gly Ala Gly Val Pro Gly
                565                 570                 575

Gly Gly Val Pro Gly Val Gly Val Pro Gly Val Gly Val Pro Gly Gly
            580                 585                 590

Gly Val Pro Gly Ala Gly Val Pro Gly Val Gly Val Pro Gly Val Gly
        595                 600                 605

Val Pro Gly Val Gly Val Pro Gly Gly Gly Val Pro Gly Ala Gly Val
    610                 615                 620

Pro Gly Gly Gly Val Pro Gly Trp Pro
625                 630
```